United States Patent
Yokota

(10) Patent No.: US 9,392,230 B2
(45) Date of Patent: Jul. 12, 2016

(54) ENDOSCOPIC APPARATUS AND MEASURING METHOD

(71) Applicant: Olympus Corporation, Tokyo (JP)

(72) Inventor: Masayoshi Yokota, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 484 days.

(21) Appl. No.: 13/747,821

(22) Filed: Jan. 23, 2013

(65) Prior Publication Data

US 2014/0002630 A1 Jan. 2, 2014

(30) Foreign Application Priority Data

Jun. 28, 2012 (JP) ................. 2012-145583

(51) Int. Cl.
*A62B 1/04* (2006.01)
*H04N 7/18* (2006.01)
(Continued)

(52) U.S. Cl.
CPC ............. *H04N 7/18* (2013.01); *A61B 1/0005* (2013.01); *A61B 1/00009* (2013.01); *A61B 1/00096* (2013.01); *A61B 1/00193* (2013.01); *G01B 11/245* (2013.01); *G06T 7/60* (2013.01); *G06T 2207/10068* (2013.01);
(Continued)

(58) Field of Classification Search
CPC ....... H04N 7/18; H04N 7/185; G01B 11/245; A61B 1/00009; A61B 1/0005; A61B 1/00096; A61B 1/00193; G06T 7/60; G06T 2207/10068; G06T 2207/20101; G06T 2207/30108

USPC ................................... 348/65, 45, 82, 72, 76
IPC .......................................................... A62B 1/04
See application file for complete search history.

(56) References Cited

U.S. PATENT DOCUMENTS 8,004,560 B2 8/2011 Sato et al.
2006/0176321 A1* 8/2006 Nakano et al. ................ 345/660
(Continued)

FOREIGN PATENT DOCUMENTS

JP    08123899 A    5/1996
JP    2002017667 A  1/2002
(Continued)

OTHER PUBLICATIONS

Japanese Office Action (and English translation thereof) dated May 17, 2016, issued in Japanese Application No. 2012-145583.

*Primary Examiner* — Trang U Tran
(74) *Attorney, Agent, or Firm* — Holtz, Holtz & Volek PC

(57) ABSTRACT

An endoscopic apparatus includes an image generation unit generates an image including subject images, a display unit displays the image and a control unit controls measurement of a size of a subject based on the image, the control unit performs first processing of displaying a moving image including one subject image on the display unit, second processing of, after the first processing, displaying all of subject images used for the measurement or all of images based on one subject image used for the measurement on the display unit as still images, and third processing of, after the second processing, designating a measurement point based on an instruction of a user, and measuring the size of the subject at the designated measurement point based on either an image based on all of subject images used for the measurement or all of the plurality of images based on the one subject image.

16 Claims, 14 Drawing Sheets

(51) Int. Cl.
*G01B 11/245* (2006.01)
*A61B 1/00* (2006.01)
*G06T 7/60* (2006.01)

(52) U.S. Cl.
CPC ............... *G06T 2207/20101* (2013.01); *G06T 2207/30108* (2013.01); *H04N 7/185* (2013.01)

(56) References Cited

U.S. PATENT DOCUMENTS

2006/0203087 A1* 9/2006 Kawanishi et al. ............. 348/65
2010/0128116 A1* 5/2010 Sato et al. ...................... 348/65
2010/0208046 A1 8/2010 Takahashi

FOREIGN PATENT DOCUMENTS

| JP | 2005-348870 A | 12/2005 |
| JP | 2007215646 A | 8/2007 |
| JP | 2009-198787 A | 9/2009 |
| JP | 4383500 B2 | 10/2009 |
| JP | 4409625 B2 | 11/2009 |
| JP | 2009271542 A | 11/2009 |
| JP | 2010-128354 A | 6/2010 |

* cited by examiner

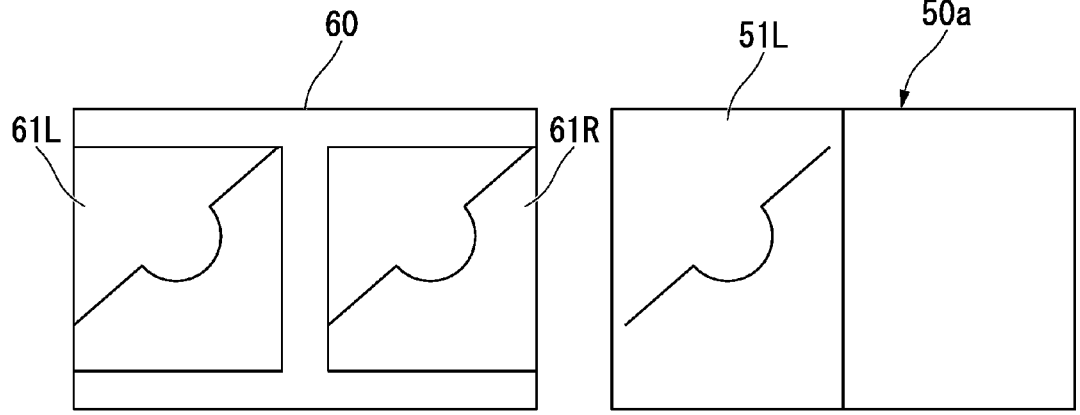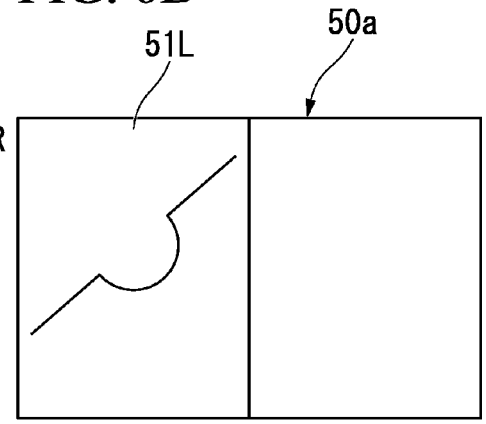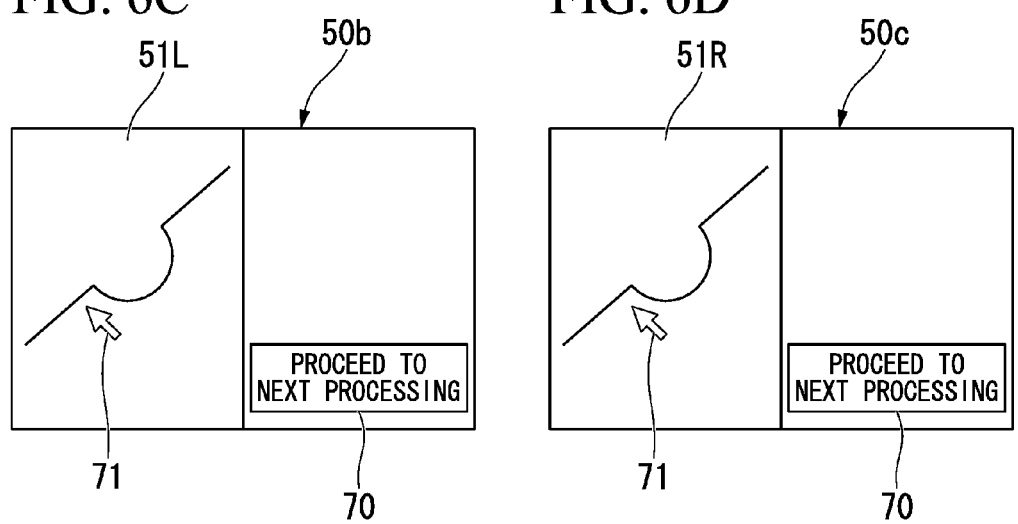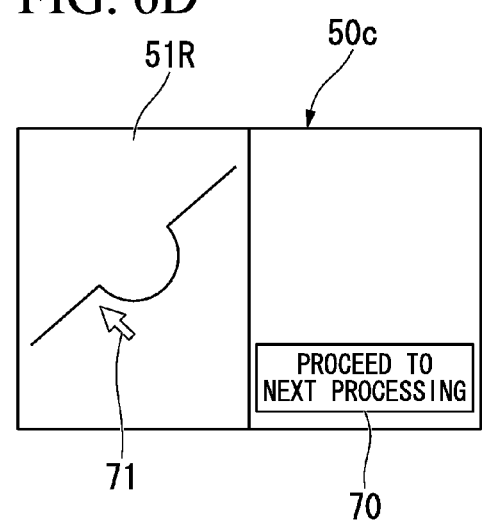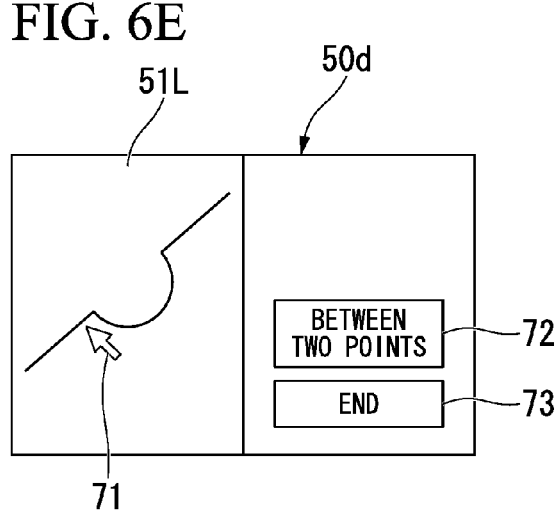

ENDOSCOPIC APPARATUS AND MEASURING METHOD

BACKGROUND OF THE INVENTION

1. Field of the Invention

The present invention relates to an endoscopic apparatus having a measuring function and a measuring method.

This application claims priority to and the benefits of Japanese Patent Application No. 2012-145583 filed on Jun. 28, 2012, the disclosure of which is incorporated herein by reference in its entirety.

2. Description of Related Art

When boilers, turbines, engines, chemical plants, etc. are tested, an industrial endoscope is widely used to observe internal damage or corrosion. In the industrial endoscope, to make it possible to observe and test a variety of observation objects, a plurality of types of optical adapters are prepared, and a distal end portion of the endoscope is configured in an exchangeable way.

One of the optical adapters is an optical adapter for stereo measurement which has two optical systems for forming two left and right subject images corresponding to different points of view. An endoscopic apparatus that uses an optical adapter for stereo measurement and realizes three-dimensional measurement based on the stereo measurement using a triangulation principle is set forth in Japanese Unexamined Patent Application, First Publication No. 2005-348870.

Endoscopic apparatuses, each of which displays an image including only some of many subject images, are set forth in Japanese Unexamined Patent Application, First Publication Nos. 2009-198787 and 2010-128354.

An endoscopic apparatus that makes it possible to ascertain the validity of results measured by a user is set forth in Japanese Patent No. 4409625.

SUMMARY OF THE INVENTION

According to a first aspect of the present invention, an endoscopic apparatus includes an image generation unit configured to generate an image including one or more subject images, a display unit configured to display the image; and a control unit configured to control measurement of a size of a subject based on the image, wherein the control unit configured to perform first processing of displaying a moving image including one subject image on the display unit, second processing of, after the first processing, displaying all of a plurality of subject images used for the measurement or all of a plurality of images based on one subject image used for the measurement on the display unit as still images, and third processing of, after the second processing, designating a measurement point based on an instruction of a user, and measuring the size of the subject at the designated measurement point based on either an image based on all of the plurality of subject images used for the measurement or all of the plurality of images based on the one subject image used for the measurement.

According to a second aspect of the present invention, in the endoscopic apparatus according to the first aspect, wherein, in the second processing, the control unit respectively displays all of the plurality of subject images used for the measurement on the display unit in time series as the still images.

According to a third aspect of the present invention, in the endoscopic apparatus according to the first aspect, wherein, in the second processing, the control unit respectively displays all of the plurality of images based on the one subject image used for the measurement on the display unit in time series as the still images.

According to a fourth aspect of the present invention, in the endoscopic apparatus according to the first aspect, wherein, in the second processing, the control unit simultaneously displays all of the plurality of subject images used for the measurement on the display unit as the still images.

According to a fifth aspect of the present invention, in the endoscopic apparatus according to the first aspect, wherein, in the second processing, the control unit simultaneously displays all of the plurality of images based on the one subject image used for the measurement on the display unit as the still images.

According to a sixth aspect of the present invention, in the endoscopic apparatus according to the first aspect, wherein, in the second processing, the control unit displays all of the plurality of subject images used for the measurement on the display unit at the same time as the still images after displaying all of the plurality of subject images used for the measurement on the display unit in time series as the still images respectively.

According to a seventh aspect of the present invention, in the endoscopic apparatus according to the first aspect, wherein, in the second processing, the control unit displays all of the plurality of images based on the one subject image used for the measurement on the display unit at the same time as the still images after displaying all of the plurality of images based on the one subject image used for the measurement on the display unit in time series as the still images respectively.

According to an eighth aspect of the present invention, in the endoscopic apparatus according to the first aspect, wherein, in the second processing, the control unit respectively displays all of the plurality of subject images used for the measurement on the display unit in time series as the still images after displaying all of the plurality of subject images used for the measurement on the display unit at the same time as the still images.

According to a ninth aspect of the present invention, in the endoscopic apparatus according to the first aspect, wherein, in the second processing, the control unit respectively displays all of the plurality of images based on the one subject image used for the measurement on the display unit in time series as the still images after displaying all of the plurality of images based on the one subject image used for the measurement on the display unit at the same time as the still images.

According to a tenth aspect of the present invention, in the endoscopic apparatus according to the first aspect, wherein, in the second processing, the control unit displays images, which are obtained by performing image processing on all of the plurality of subject images used for the measurement, on the display unit as the still images.

According to an eleventh aspect of the present invention, in the endoscopic apparatus according to the first aspect, wherein, in the second processing, the control unit displays images, which are obtained by performing image processing on all of the plurality of images based on the one subject image used for the measurement, on the display unit as the still images.

According to a twelfth aspect of the present invention, in the endoscopic apparatus according to the tenth aspect, wherein the control unit switches whether or not to perform the image processing.

According to a thirteenth aspect of the present invention, a measuring method includes a first step of displaying a moving image including one subject image photographed by an endoscopic apparatus on a display unit, a second step of, after the first step, displaying all of a plurality of subject images used for measurement or all of a plurality of images based on one subject image used for measurement on the display unit as still images; and a third step of, after the second step, designating a measurement point based on an instruction of a user, and measuring a size of a subject at the designated measurement point based on either an image based on all of the plurality of subject images or all of the plurality of images based on the one subject image used for measurement.

According to an fourteenth aspect of the present invention, an endoscopic apparatus includes, an image generation unit configured to generate an image including subject images; a display unit configured to display the image and a control unit configured to control measurement of a size of a subject based on the image, wherein the control unit configured to perform first processing of displaying a moving image including one subject image on the display unit, second processing of, after the first processing, displaying all of a plurality of images used for the measurement on the display unit as still images, and third processing of, after the second processing, designating a measurement point based on an instruction of a user, and measuring the size of the subject at the designated measurement point based on all of the plurality of images used for the measurement.

BRIEF DESCRIPTION OF THE DRAWINGS

FIG. 6A is a reference view showing an image in the first embodiment of the present invention.

FIG. 6B is a reference view showing an image in the first embodiment of the present invention.

FIG. 6C is a reference view showing an image in the first embodiment of the present invention.

FIG. 6D is a reference view showing an image in the first embodiment of the present invention.

FIG. 6E is a reference view showing an image in the first embodiment of the present invention.

DETAILED DESCRIPTION OF THE INVENTION

Hereinafter, embodiments of the present invention will be described with reference to the drawings.

First Embodiment

Figure 1:
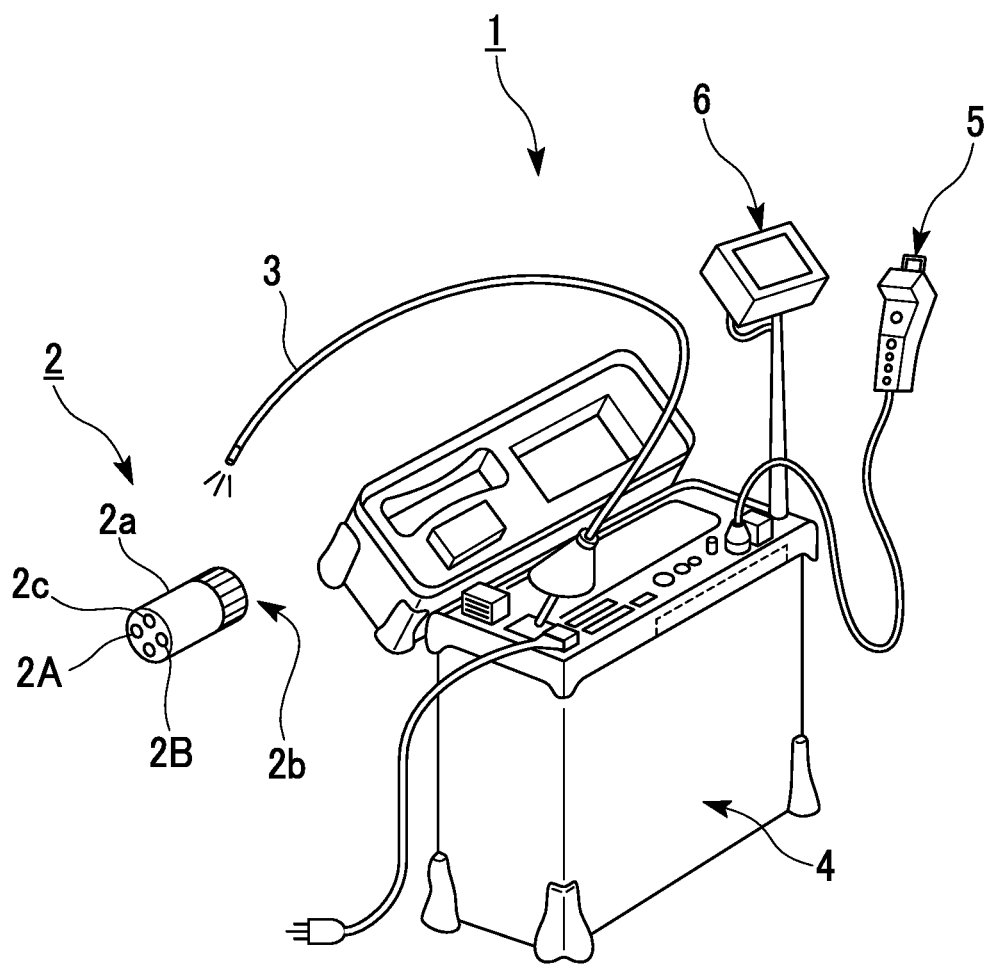
FIG. 1 is a perspective view showing an endoscopic apparatus according to a first embodiment of the present invention.
Figure 2:
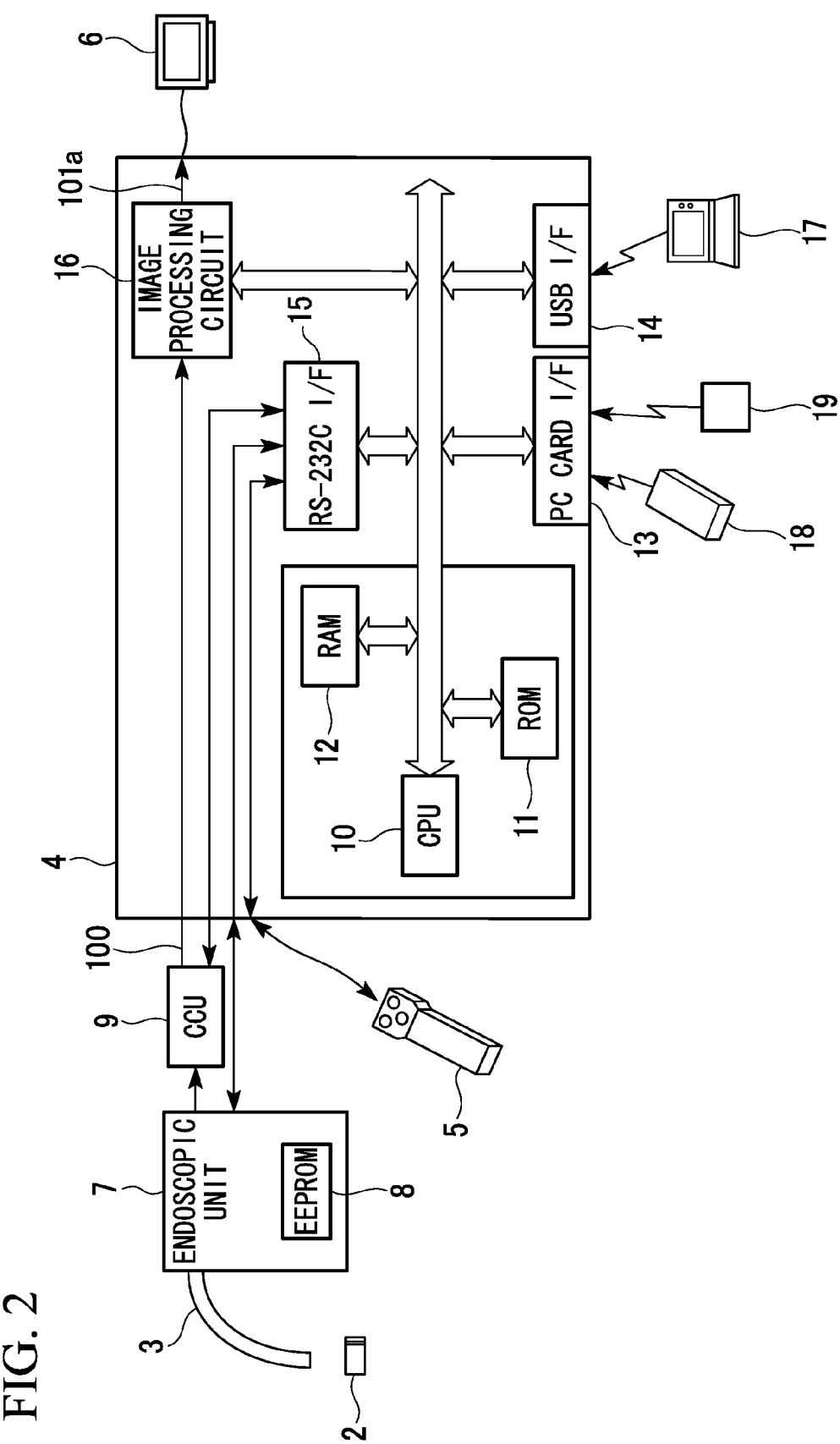
FIG. 2 is a block diagram showing a configuration of the endoscopic apparatus according to the first embodiment of the present invention.
Figure 3:
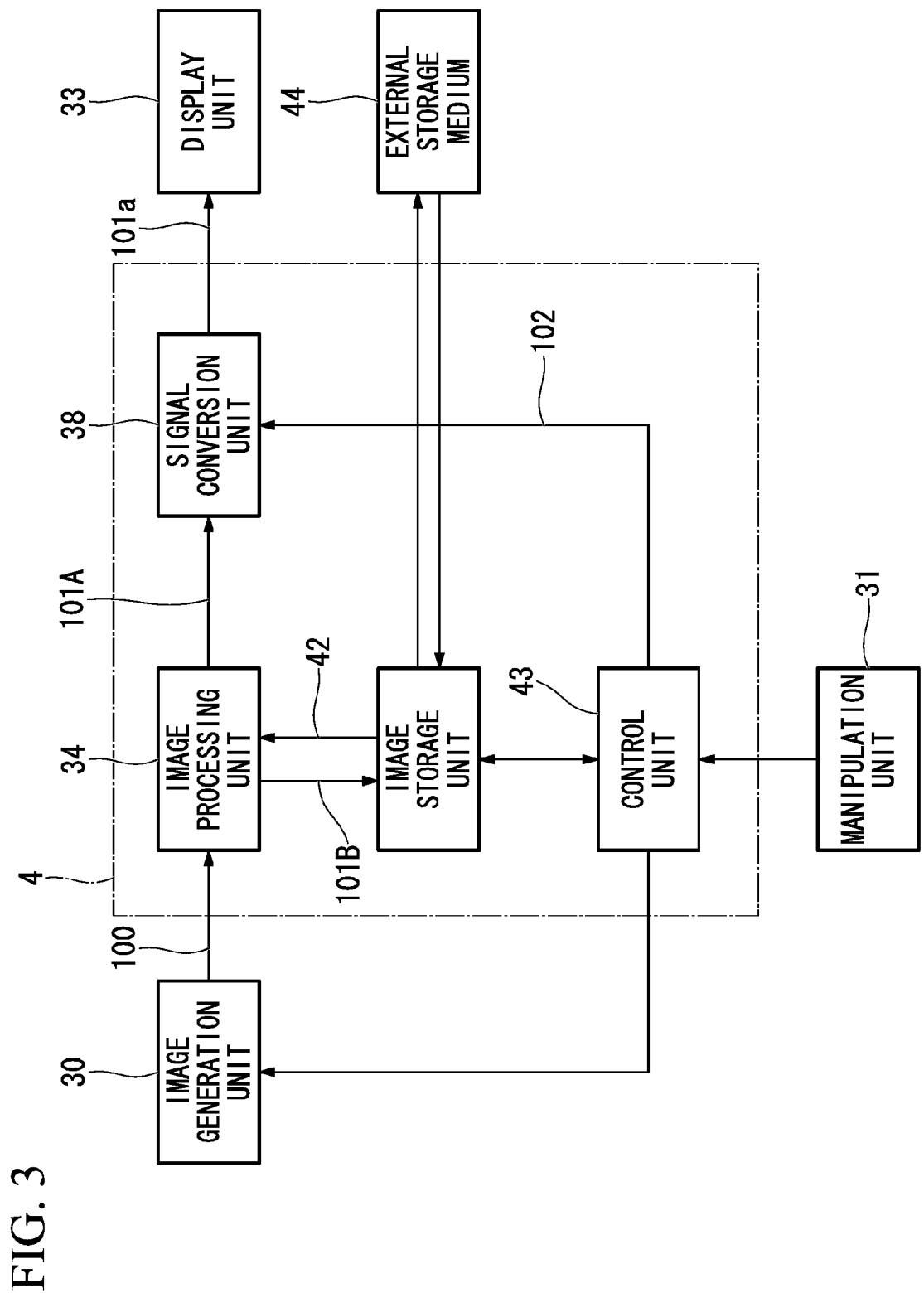
FIG. 3 is a block diagram showing a functional configuration of the endoscopic apparatus according to the first embodiment of the present invention.

First, a first embodiment of the present invention will be described. FIG. 1 shows an external appearance of an endoscopic apparatus according to the present embodiment. FIG. 2 shows a functional configuration of the endoscopic apparatus according to the present embodiment. FIG. 3 shows a functional configuration of a control unit having the endoscopic apparatus according to the present embodiment. The endoscopic apparatus 1 of the present embodiment takes an image of a test object that is a subject serving as a test target, and carries out various types of observation and measurement by exchanging an optical adapter at a distal end of an endoscope insertion part, by properly selecting a built-in measuring program, or by properly adding a measuring program, in order to carry out measurement using the image. Hereinafter, a case in which stereo measurement is carried out as an example of the measurement will be described.

As shown in FIGS. 1 and 2, the endoscopic apparatus 1 includes an optical adapter for stereo measurement 2, an endoscope insertion part 3, an endoscopic unit 7, a camera control unit (CCU) 9, a liquid crystal monitor (display unit) 6, a remote controller 5, and a control unit 4. The optical adapter for stereo measurement 2 has a structure in which object lenses 2A and 2B disposed to be spaced a predetermined distance apart from each other are disposed in a main body of an approximately cylindrical adapter 2a in order to obtain an image having parallax, and is detachably mounted on the distal end of the endoscope insertion part 3, for instance, by a mount unit 2b in which internal threads are formed.

Positions of the object lenses 2A and 2B are different between a direct-viewing type having a field of view in an axial direction of the optical adapter for stereo measurement 2 and a side-viewing type having a field of view in a lateral direction of the optical adapter for stereo measurement 2. In the present embodiment, positions of the object lenses 2A and 2B are shown as the direct viewing type. For this reason, the object lenses 2A and 2B are disposed adjacent to openings formed in a distal end face in a state in which an optical axis is directed in the axial direction of the optical adapter for stereo measurement 2. Further, the distal end face of the optical adapter for stereo measurement 2 is provided with an illumination window 2c that outputs illuminating light guided into the adapter main body 2a toward a test object.

The endoscope insertion part 3 takes an image of a portion of a measurement target in a state in which it is inserted into the test object, and outputs an imaging signal to the control unit 4. A distal end of the endoscope insertion part 3 that can be curved is configured to be provided with a mount unit that is common to a plurality of optical adapters such as the optical adapter for stereo measurement 2, and to allow each optical adapter to be exchangeably mounted. Although not shown, at an inside of the distal end, an image pick up element such as a charged coupled device (CCD), which images formed by a plurality of object lenses of the optical adapter are taken is disposed, and a light guide applying the illuminating light to the test object is provided.

The endoscope insertion part 3 is formed in a shape of an elongated tube that can be curved from a distal end to a proximal end thereof. A signal line of the image pickup element, a light guide main body, and a wire mechanism for manipulating curvature of the distal end (none of which is shown) are disposed inside the endoscope insertion part 3. When the optical adapter for stereo measurement 2 is mounted on the endoscope insertion part 3, a pair of images having parallax (hereinafter referred to as "parallactic images") are simultaneously obtained by the image pickup element, and an imaging signal is adapted to be transmitted to the CCU 9 by the signal line inside the endoscope insertion part 3.

The endoscopic unit 7 is a device that includes an illuminating light source generating the illuminating light guided to the light guide of the endoscope insertion part 3, an electric curvature driving unit of the wire mechanism, and an electrically erasable programmable read-only memory (EEPROM) 8 for storing control parameters driving the electric curvature driving unit, and is mounted in the control unit 4 in a state in which it is connected to the proximal end of the endoscope insertion part 3.

The CCU 9 controls an imaging operation of the image pickup element provided to the endoscope insertion part 3, converts an imaging signal obtained by the image pickup element into an image signal such as a National Television System Committee (NTSC) signal, and outputs the converted signal to the control unit 4 as an input image signal 100 (see FIG. 3).

The liquid crystal monitor 6 displays an image of the test object and other information of the image based on a display image signal 101a (see FIG. 3) output from the control unit 4. The image and information are respectively displayed independently or jointly as needed. When the stereo measurement is taken as in the present embodiment, the display image signal 101a corresponds to an image including one or both of the parallactic images.

The other information displayed on the liquid crystal monitor 6 includes, for example, information input from a manipulation unit such as a remote controller 5 to be described below, a manipulation menu, and a manipulation graphical user interface (GUI). Further, the other information includes an image of a cursor used during the measurement, and measurement information 102 (see FIG. 3) including a measurement result. Hereinafter, an image including information associated with the manipulation is referred to as a manipulation image.

The remote controller 5 is a manipulation unit for a user performing a variety of manipulation inputs on the endoscopic apparatus 1, and is connected to the control unit 4. The manipulation inputs which the user performs via the remote controller 5 include, for example, manipulation related to ON/OFF of a power supply, manipulation related to the imaging operation, manipulation related to the illumination, manipulation of curvature driving of the endoscope insertion part 3, manipulation related to the measurement, manipulation of selecting image processing for the image displayed on the liquid crystal monitor 6, manipulation of recording an image on an external storage medium, and manipulation of reading out the image recorded on the external storage medium. These manipulations are adapted to be able to be performed via a user interface, arbitrarily.

For example, although not shown, a joystick, a lever switch, a freeze switch, a store switch, and a measurement fulfillment switch are provided to the remote controller 5. A user performs selection and input of the manipulation menu or direct input of an instruction via these, or manipulates the GUI displayed on the liquid crystal monitor 6. Thereby, a variety of manipulation inputs may be performed.

The control unit 4 has control over the entire endoscopic apparatus 1 including the image processing of the imaged image and the measurement processing. In the present embodiment, as shown in FIG. 2, the control unit 4 is made up of a central processing unit (CPU) 10, a read-only memory (ROM) 11, a random access memory (RAM) 12, a variety of input/output interfaces, and an image processing circuit 16.

The CPU 10 executes a control program stored in the ROM 11 or the external storage medium 44 (see FIG. 3) by loading the control program into the RAM 12, and performs an operation of each function to be described below. The input/output interfaces include, for example, a recommended standard 232 version C (RS-232C) interface 15, a personal computer (PC) card interface 13, and a universal serial bus (USB) interface 14.

The RS-232C interface 15 communicates for operation control among the remote controller 5, the endoscopic unit 7, and the CCU 9. The PC card interface 13 is used to connect a PC card complying with Personal Computer Memory Card International Association (PCMCIA). In the present embodiment, a typically removable external storage medium is connected to the PC card interface 13, and the information related to the measurement result and the image information are stored via the PC card interface 13.

For this reason, a variety of memory cards, for instance a PCMCIA memory card 18 and a flash memory card 19, which use a flash memory as an external storage medium are mounted on the PC card interface 13.

The USB interface 14 is used to connect a USB device. In the present embodiment, the USB interface 14 is provided to removably connect the personal computer 17. When the personal computer 17 is connected to the USB interface 14, various pieces of information are transmitted and received between the control unit 4 and a storage device inside the personal computer 17 via the PC card interface 13.

When the personal computer 17 is connected, the personal computer 17 may function as the liquid crystal monitor 6, the remote controller 5, and the external storage medium which are connected to the control unit 4. For this reason, for example, the control related to the measurement, the image processing, and the image display may be performed using resources of the personal computer 17 as needed.

The image processing circuit 16 performs designated image processing on an input image signal 100 (see FIG. 3) supplied from the CCU 9 via the remote controller 5, thereby generating output image signals 101A and 101B (see FIG. 3). Further, the image processing circuit 16 combines the output image signals 101A and 101B with a manipulation image or measurement information 102 (see FIG. 3) generated by the CPU 10 as needed, converts the combined result into, for instance, an NTSC signal to display an image on the liquid crystal monitor 6, and outputs the converted signal to the liquid crystal monitor 6 as a display image signal 101*a*.

Next, a principal functional configuration of the endoscopic apparatus 1 will be described with reference to FIG. 3. The endoscopic apparatus 1 includes an image generation unit 30, a manipulation unit 31, and a display unit 33, and further includes an image processing unit 34, a signal conversion unit 38, an image storage unit 42, and a control unit 43 inside the control unit 4.

The image generation unit 30 corresponds to the image pickup element inside the endoscope insertion part 3, the endoscopic unit 7, and the CCU 9, and generates an image including two subject images, which are formed simultaneously by two optical systems (object lenses 2A and 2B) of the optical adapter for stereo measurement 2, as parallactic images. The manipulation unit 31 is installed such that a user performs manipulation input such as measurement, and corresponds to the remote controller 5. The display unit 33 corresponds to the liquid crystal monitor 6, and displays an image based on the display image signal 101*a*. The personal computer 17 may function as the manipulation unit 31 and the display unit 33.

Image information for one frame, on which preprocessing such as brightness level adjustment or noise removal processing is performed by the CCU 9 and which includes a pair of parallactic images, is input from the image generation unit 30 to the image processing unit 34 as the input image signal 100. The preprocessing may be performed as the image processing by the image processing unit 34.

The image processing part 34 and the signal conversion unit 38 correspond to the image signal processing circuit 16. The image processing unit 34 is configured to perform the image processing on the input image signal 100 that has been input, to generate an output image signal 101A, to output the generated signal to the signal conversion unit 38, to simultaneously generate an output image signal 101B, and to output the generated signal to the image storage unit 42. Further, the image processing unit 34 processes the input image signal 100 so as to extract the parallactic image composed of one subject image from the image including the two subject images that are simultaneously formed by the two optical systems of the optical adapter for stereo measurement 2 as required, and then outputs the processed signal to the signal conversion unit 38 as the output image signal 101A. Further, the output image signals 101A and 101B are not limited to different signals, and they may be the same signals on which the same image processing is performed.

The signal conversion unit 38 outputs the output image signal 101A, which is output from the image processing unit 34, to the display unit 33 as the display image signal 101*a*. In this case, the signal conversion unit 38 may combine other image data such as a manipulation image with the display image signal 101*a* as needed. Further, when the measurement information 102 is output from the control unit 43, the signal conversion unit 38 may generate the display image signal 101*a* in combination with the measurement information 102.

The image storage unit 42 corresponds to the RAM 12, and stores the output image signal 101B, which is output from the image processing unit 34, as still-image data. Further, when manipulation input of recording processing is performed via the manipulation unit 31, the still-image data is read out of the image storage unit 42 under control of the control unit 43, is output to the external storage medium 44, and is stored in the external storage medium 44. The external storage medium 44 corresponds to the personal computer 17, the PCMCIA memory card 18, and the flash memory card 19.

The control unit 43 corresponds to the CPU 10. The control unit 43 reads out a control program stored in the ROM 11 or the external storage medium 44, loads the read control program into the RAM 12, and executes commands set forth in the control program, thereby controlling each unit in the endoscopic apparatus 1. When the manipulation input of the measurement processing is performed via the manipulation unit 31, the control unit 43 performs the measurement processing based on stereo measurement using the still-image data stored in the image storage unit 42, and generates a measuring GUI image required for the manipulation input of measurement. For example, when a measurement point is input on a display image of the liquid crystal monitor 6 via the manipulation unit 31, the control unit 43 acquires positional information about corresponding points of the parallactic images corresponding to the measurement point by performing matching processing based on respective brightness information, and calculates the acquired information in terms of three-dimensional position coordinates based on a triangulation principle.

Along with the measuring GUI image, the cursor displayed on the display unit 33, the information of the measurement point, and the measured result are output as the measurement information 102 from the control unit 43 to the signal conversion unit 38, and are combined into the output image signal 101A by the signal conversion unit 38.

The control program of the endoscopic apparatus 1 may be recorded on a computer readable recording medium, and the control program recorded on this recording medium may be executed by reading it into a computer other than the endoscopic apparatus 1. For example, the personal computer 17 may read and execute the control program and, according to the control program, transmit control information for controlling the endoscopic apparatus 1 to the endoscopic apparatus 1, and operate the endoscopic apparatus 1 in an image display mode or in an image confirmation mode. Here, the term "computer" also includes a home page providing environment (or a display environment) if it uses a world wide web (WWW) system. Further, the term "computer readable recording medium" refers to a portable medium such as a flexible disk, a magnetic optical disc, a ROM, a CD-ROM, a DVD-ROM, or a flash memory, or a storage device such as a hard disk mounted in a computer. Furthermore, the term "computer readable recording medium" also includes one that holds a program for a predetermined time like a volatile memory (RAM) inside a computer system becoming a server or a client when the program is transmitted via a network such as the Internet or a communication line such as a telephone line.

Further, the aforementioned program may be transmitted from a computer in whose storage device this program is stored to another computer via a transmission medium or by a transmitted wave of the transmission media. Here, the "transmission medium" transmitting the program refers to a medium that functions to transmit information, like a network (communication network) such as the Internet or a communication line (communication wire) such as a telephone line. Further, the aforementioned program may be designed to realize a part of the above function. Furthermore, the program may be designed to be able to realize the above function by combination with a program recorded previously on a computer, and a so-called differential file (differential program).

Figure 4:
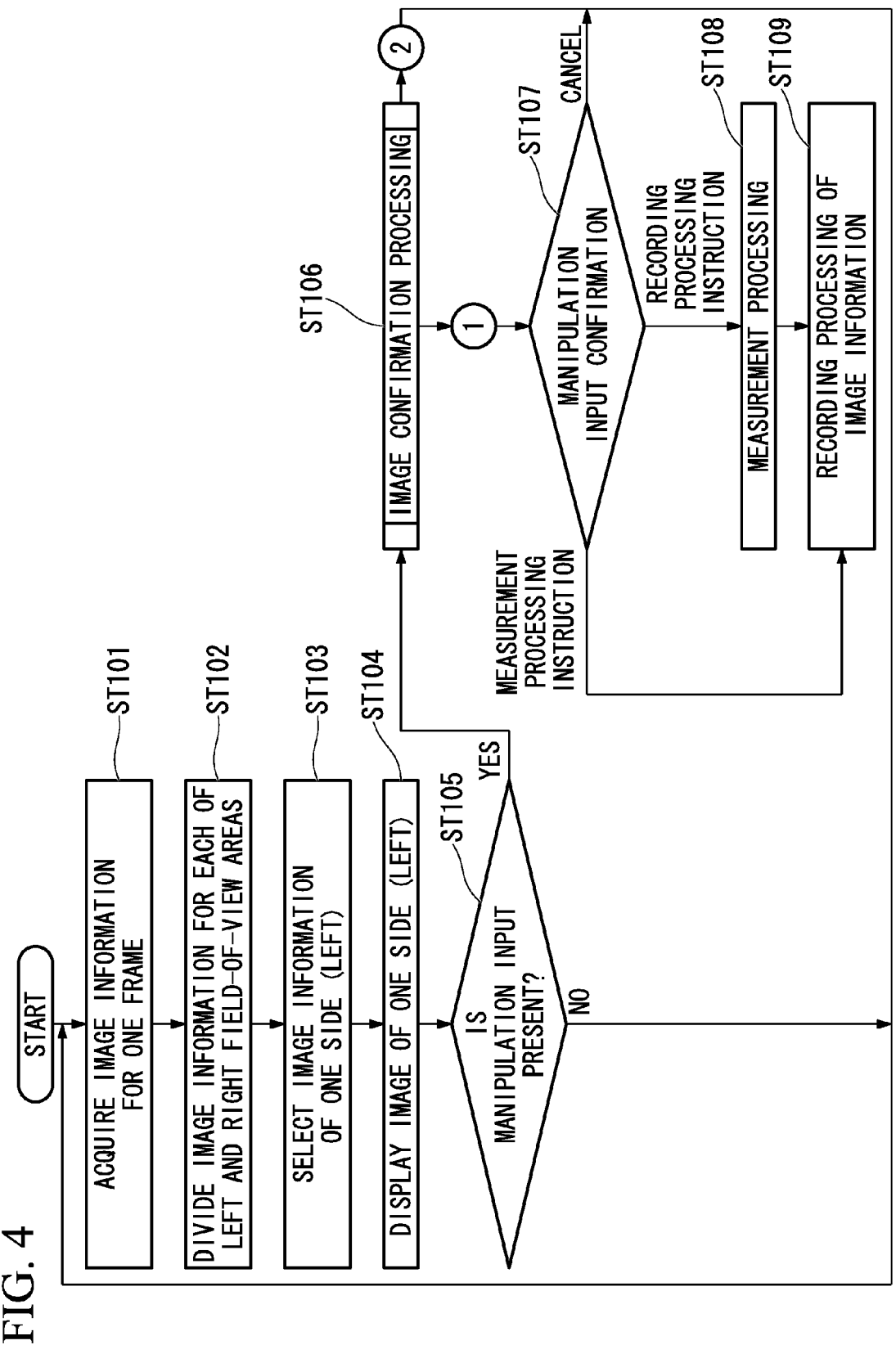
FIG. 4 is a flow chart showing sequences of an operation of the endoscopic apparatus according to the first embodiment of the present invention.
Figure 5:
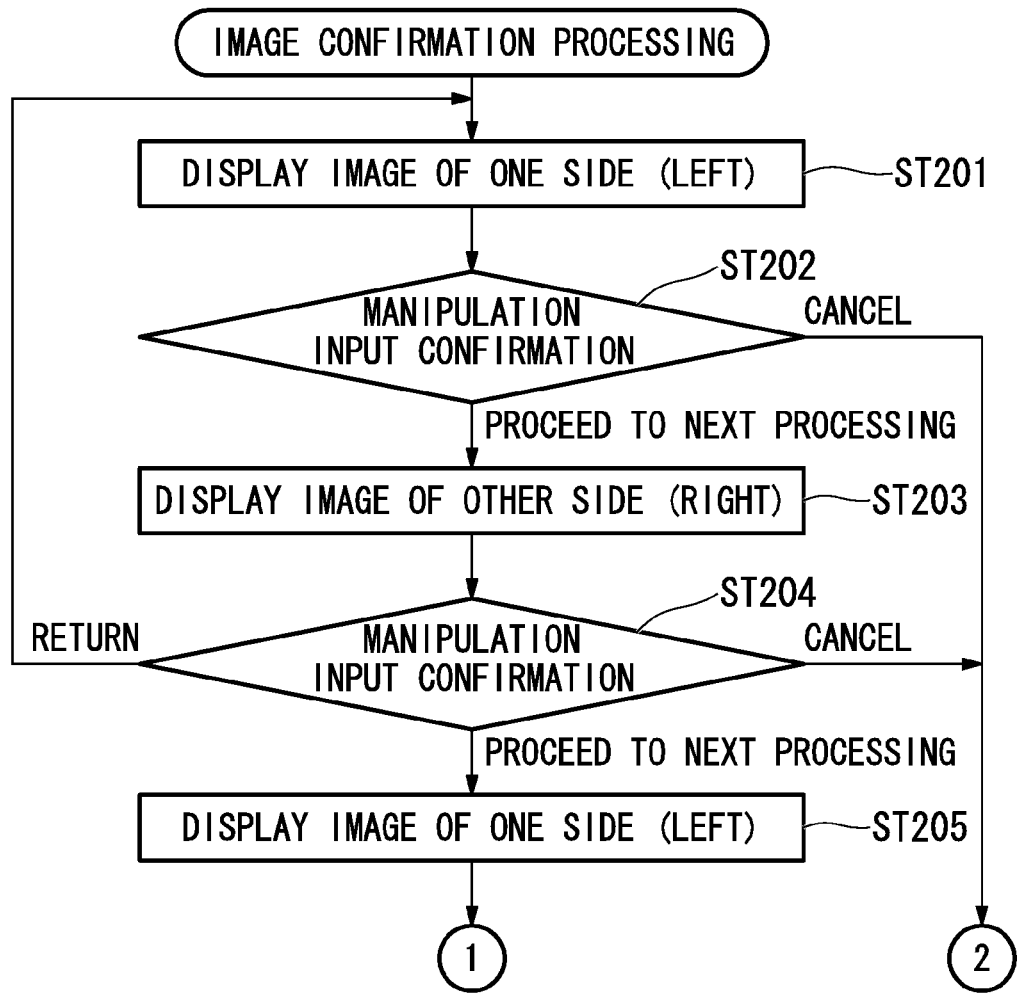
FIG. 5 is a flow chart showing sequences of an operation of the endoscopic apparatus according to the first embodiment of the present invention.

Next, an operation of the endoscopic apparatus 1 will be described. FIGS. 4 and 5 show sequences of the operation of the endoscopic apparatus 1. When a power supply is applied, the endoscopic apparatus 1 operates in an image display mode in which the images acquired through the optical adapter for stereo measurement 2 are displayed on the liquid crystal monitor 6. Further, when manipulation input is performed via the manipulation unit 31, the endoscopic apparatus 1 operates in an image confirmation mode in which all the images used for measurement are confirmed by a user. During operation in the image confirmation mode, all the images used for measurement are completely confirmed, and the manipulation input is performed via the manipulation unit 31. Then, the endoscopic apparatus 1 operates in various processing modes corresponding to the manipulation inputs. Hereinafter, as the various processing modes, modes of performing measurement processing and recording processing of image information will be described as an example.

In the image display mode, a user inserts the endoscope insertion part 3 mounting the optical adapter for stereo measurement 2 into a test object. Image information including two subject images formed on the image pickup element through the optical adapter for stereo measurement 2 is output to the control unit 4 through the CCU 9 as the input image signal 100.

As shown in FIG. 4, in ST101, the control unit 4 acquires image information for one frame from the image generation unit 30. That is, the input image signal 100 is output from the image generation unit 30 to the image processing unit 34 of the control unit 4 under control of the control unit 43, and the input image signal 100 for one frame is acquired as the image information by the image processing unit 34.

Subsequently, in ST102, the image processing unit 34 divides the input image signal 100 for one frame under control of the control unit 43. That is, the image processing unit 34 divides the image information acquired from the image generation unit 30 into field-of-view areas. Specifically, the image processing unit 34 divides the image information into a field-of-view area including left subject image among two left and right subject images and a field-of-view area including right subject image among two left and right subject images. In this case, the image may be divided in two in the middle thereof, or the images of only the field-of-view areas may be extracted using information related to positions of two field-of-view areas obtained by previous measurement. The two divided pieces of image information are output to the image storage unit 42 as the output image signal 101B, and are stored in the image storage unit 42.

Next, in ST103, under control of the control unit 43, the image processing unit 34 outputs an image signal for one frame corresponding to one (as an example, in the present embodiment, assumed to be the parallactic image corresponding to the left field-of-view area) of the two divided pieces of image information to the signal conversion unit 38 as the output image signal 101A.

Subsequently, in ST104, under control of the control unit 43, the signal conversion unit 38 performs processing on the output image signal 101A that has been input thereto such as changing an image size to a size at which the display unit 33 can display an image, and outputs the processed output image signal 101A to the display unit 33 as the display image signal 101*a*. The display unit 33 displays an image based on the display image signal 101*a*. Thereby, the image including the parallactic image corresponding to the left field-of-view area is displayed on the display unit 33.

FIGS. 6A, 6B, 6C, 6D, and 6E show images that are generated and displayed by the endoscopic apparatus 1 of the present embodiment. FIG. 6A shows an image that is generated by the image generation unit 30 and has not been divided on each field-of-view area by the image processing unit 34. The image 60 is constituted of an image area formed on top and bottom and middle thereof in an I shape, and two approximately rectangular image areas outside of the I-shaped image area. The left image area is constituted of a parallactic image 61L corresponding to a left subject image of the two subject images simultaneously formed by the two optical systems of the optical adapter for stereo measurement 2. The right image area is constituted of a parallactic image 61R corresponding to a right subject image of the two subject images simultaneously formed by the two optical systems of the optical adapter for stereo measurement 2.

FIG. 6B shows an image displayed on the display unit 33 in ST104. A parallactic image 51L corresponding to a left subject image of the two subject images simultaneously formed by the two optical systems of the optical adapter for stereo measurement 2 is included in an image 50*a*. The parallactic image 51L may be enlarged and displayed. In this case, the image processing unit 34 performs enlargement processing on an image signal for one frame corresponding to one of the two divided pieces of image information, and outputs the processed image signal to the signal conversion unit 38 as the output image signal 101A.

When the processing of ST104 is completed, processing of ST105 is performed. In ST105, the control unit 43 determines whether or not manipulation input is performed via the manipulation unit 31. When the manipulation input is performed, processing of ST106 is performed. In contrast, when the manipulation input is not performed, the processing of ST101 is performed, and the above processing is performed again on the next image information for one frame. In other words, when the manipulation input is not generated, an image display mode of displaying a time series of one-frame images undergoing the image processing on the display unit 33 in real time as moving images is realized. While observing the displayed image, a user adjusts the curvature of the distal end of the endoscope insertion part 3 using the remote controller 5 such that a desired measurement portion of the test object is fitted in the image.

Next, processing (image confirmation processing) performed in ST106 will be described in detail. FIG. 5 shows sequences of the processing performed in ST106. As shown in FIG. 5, in ST201, under control of the control unit 43, the image processing unit 34 outputs an image signal for one frame corresponding to one (as an example, in the present embodiment, assumed to be the parallactic image corresponding to the left field-of-view area) of the two pieces of image information stored in the image storage unit 42 to the signal conversion 38 as the output image signal 101A. Under control of the control unit 43, the signal conversion unit 38 performs processing on the output image signal 101A that has been input thereto such as changing an image size to a size at which the display unit 33 can display an image, and outputs the processed output image signal 101A to the display unit 33 as the display image signal 101*a*. The display unit 33 displays an image based on the display image signal 101*a*. Thereby, the image including the parallactic image corresponding to the left field-of-view area is displayed on the display unit 33. The parallactic image that is displayed in ST201 and corresponds to the left field-of-view area is the same as the parallactic image that is previously displayed in ST104 and corresponds to the left field-of-view area.

FIG. 6C shows the image displayed on the display unit 33 in ST201. A parallactic image 51L corresponding to the left subject image of the two subject images simultaneously formed by the two optical systems of the optical adapter for stereo measurement 2, a button 70 for manipulation input, and a cursor 71 for a user manipulating the button 70 are included in an image 50*b*. As described above, the parallactic image 51L in the image 50*b* is the same as the parallactic image 51L in the image 50*a* that is previously displayed in ST104. Information such as a letter indicating whether the parallactic image corresponding to either of the left and right field-of-view areas is displayed may be displayed along with the parallactic image.

Subsequently, in ST202, the control unit 43 determines whether or not the manipulation input is performed via the manipulation unit 31. The image (still image) displayed in ST201 is not changed until the manipulation input is performed. In ST202, when the button 70 referring to proceeding to the next processing is manipulated, processing of ST203 is performed.

In ST203, under control of the control unit 43, the image processing unit 34 outputs an image signal for one frame corresponding to one (as an example, in the present embodiment, assumed to be the parallactic image corresponding to the right field-of-view area) of the two pieces of image information stored in the image storage unit 42 to the signal conversion unit 38 as the output image signal 101A. Afterwards, an image is displayed on the display unit 33 by the aforementioned processing. Thereby, the image including the parallactic image corresponding to the right field-of-view area is displayed on the display unit 33. Information such as a letter indicating whether the parallactic image corresponding to either of the left and right field-of-view areas is displayed may be displayed along with the parallactic image.

FIG. 6D shows the image displayed on the display unit 33 in ST203. A parallactic image 51R corresponding to the right subject image of the two subject images simultaneously formed by the two optical systems of the optical adapter for stereo measurement 2, a button 70 for manipulation input, and a cursor 71 for a user manipulating the button 70 are included in a image 50*c*.

Subsequently, in ST204, the control unit 43 determines whether or not the manipulation input is performed via the manipulation unit 31. The image (still image) displayed in ST203 is not changed until the manipulation input is performed. In ST204, when the button 70 referring to proceeding to the next processing is manipulated, processing of ST205 is performed.

As in ST201, in ST205, the image including the parallactic image corresponding to the left field-of-view area is displayed on the display unit 33. In ST205, the image including the parallactic image corresponding to the right field-of-view area may be displayed. When the processing of ST205 is completed, the processing of ST106 (image confirmation processing) is completed, and processing of ST107 is performed. Further, in ST204, when the manipulation input referring to returning to the previous processing is performed, the processing of ST201 is performed, and the image including the parallactic image corresponding to the left field-of-view area is displayed on the display unit 33 again. Further, in ST202 and ST204, when the manipulation input referring to stopping confirmation of the image is performed, the processing of ST101 is performed, and the endoscopic apparatus 1 operates in the image display mode.

In ST107, the control unit 43 determines whether or not the manipulation input is performed via the manipulation unit 31. When the manipulation input is performed, the control unit 43 performs each processing according to the manipulation input. When the manipulation input referring to a measurement instruction is performed, processing of ST108 (measurement processing) is performed. In ST108, under control of the control unit 43, the image processing unit 34 outputs an image signal for one frame corresponding to one (as an example, in the present embodiment, assumed to be the parallactic image corresponding to the left field-of-view area) of the two pieces of image information stored in the image storage unit 42 to the signal conversion unit 38 as the output image signal 101A. Afterwards, an image is displayed on the display unit 33 by the aforementioned processing. Thereby, the image including the parallactic image corresponding to the left field-of-view area is displayed on the display unit 33.

FIG. 6E shows the image displayed on the display unit 33 in ST108. A parallactic image 51L corresponding to the left subject image of the two subject images simultaneously formed by the two optical systems of the optical adapter for stereo measurement 2, a button 72 for manipulation input for a user instructing a start of calculation processing of measurement after input of a measurement point, a button 73 for manipulation input for a user instructing an end of measurement processing, and a cursor 71 for a user designating the measurement point or manipulating the buttons 72 and 73 are included in an image 50*d*. In FIG. 6E, the parallactic image corresponding to the left field-of-view area is displayed. However, the parallactic image corresponding to the right field-of-view area may be displayed. Further, the button for manipulation input in FIG. 6E is given as an example. Thus, buttons for designating types of the calculation processing of measurement (a distance between two points, a depth, an area, etc.) may be present.

Further, in ST108, the control unit 43 reads an image signal for one frame corresponding to the two pieces of image information out of the image storage unit 42, and designates the measurement point in one of the two pieces of image information based on the instruction of the measurement point input via the manipulation unit 31. Furthermore, the control unit 43 finds a position of a point (corresponding point) corresponding to the measurement point in the other image information, calculates three-dimensional coordinates on a subject from the position of the point corresponding to the measurement point, and measures a size (a distance between two points, a depth, an area, etc.) of the subject at the measurement point.

In ST107, when the manipulation input instructing recording of the image information is performed, processing of ST109 (recording processing of the image information) is performed. In ST109, under control of the control unit 43, an image signal for one frame corresponding to the two pieces of image information is read out of the image storage unit 42, is output to the external storage medium 44, and is stored in the external storage medium 44. When the image information is recorded, the image including the two parallactic images corresponding to the left and right field-of-view areas as in FIG. 6A may be recorded, or the two parallactic images corresponding to the left and right field-of-view areas may be assumed to be separate images, and be recorded with these images associated with each other.

Further, in ST107, when the manipulation input referring to performing neither the measurement nor the recording of the image information is performed, the processing of ST101 is performed, and the endoscopic apparatus 1 operates in the image display mode.

As described above, except when the image is confirmed (ST106), the parallactic image corresponding to only one of the left and right field-of-view area is displayed. For this reason, when the two parallactic images corresponding to the left and right field-of-view areas are displayed at the same time, a user frequently shifts his/her eyes between the two parallactic images. Thereby, the visibility does not deteriorate.

Further, before the user inputs the measurement point, the user may transfer the operation mode of the endoscopic apparatus to the image confirmation mode by means of simple manipulation input. In the image confirmation mode, all the parallactic images used for the measurement are confirmed by the processing of ST201 and the processing of ST203. When both the processing of ST201 and the processing of ST203 are completed, the processing can be transferred to the measurement processing. When the image is confirmed, the user may confirm all the parallactic images at his/her own pace in a state in which the image is in a still state. As such, even when the measurement is performed in a state in which the image including only one of the two parallactic images is displayed in the event of the measurement, the validity of the measurement result can be easily confirmed before the measurement is performed. Further, when the user determines that the displayed image is not suitable for the measurement during confirmation of the image, the user may transfer the operation mode of the endoscopic apparatus to the image confirmation mode by means of simple manipulation input, and photograph the image again. As such, testing efficiency is improved.

When the test object is tested by the endoscopic apparatus, the distal end of the endoscope insertion part often approaches the test object to observe the test object, and the left and right parallax is increased. When the left and right parallax is increased, the validity of the measurement result is easily deteriorates. For this reason, in the endoscopic apparatus in which the image including the two parallactic images is automatically displayed when the validity of the measurement result is low, the image including the two parallactic images is frequently displayed, and the visibility during the measurement deteriorates. In contrast, in the endoscopic apparatus of the present embodiment, since it is unnecessary to display the image including the two parallactic images during the measurement, the visibility during the measurement does not deteriorate.

After the test object is observed by the endoscopic apparatus, the measurement is not always performed in the field, but the image is only photographed in the field, and then the measurement is performed while the image is being reproduced. Using this method, the test may be performed. In a case in which the test is performed by this method, when a photographed image is not suitable for the measurement, this causes trouble of returning to the field to photograph the image again. In contrast, when the test is performed using the endoscopic apparatus of the present embodiment, all the parallactic images used for the measurement are confirmed by the processing of ST201 and the processing of ST203, and then the image information is recorded in ST109. For this reason, it is possible to reduce the mistake of recording images unsuitable for the measurement, and thus to previously prevent the trouble of returning to the field to photograph the image again.

Figure 7:
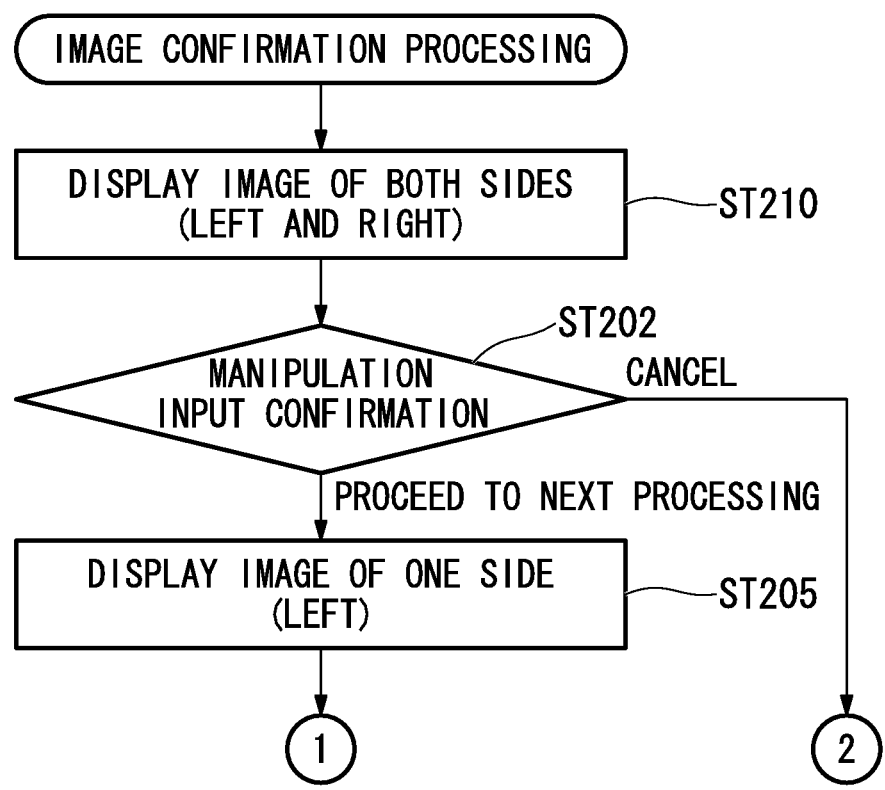
FIG. 7 is a flow chart showing sequences of an operation of the endoscopic apparatus according to the first embodiment of the present invention.

Next, a modification of the present embodiment will be described. FIG. 7 shows another example of the sequences of the processing performed in ST106. In ST210, under control of the control unit 43, the image processing unit 34 outputs an image signal for one frame corresponding to one of the two pieces of image information stored in the image storage unit 42 to the signal conversion unit 38 as the output image signal 101A. Afterwards, an image is displayed on the display unit 33 by the aforementioned processing. Thereby, the image including the parallactic images corresponding to the left and right field-of-view areas is displayed on the display unit 33.

Figure 8:
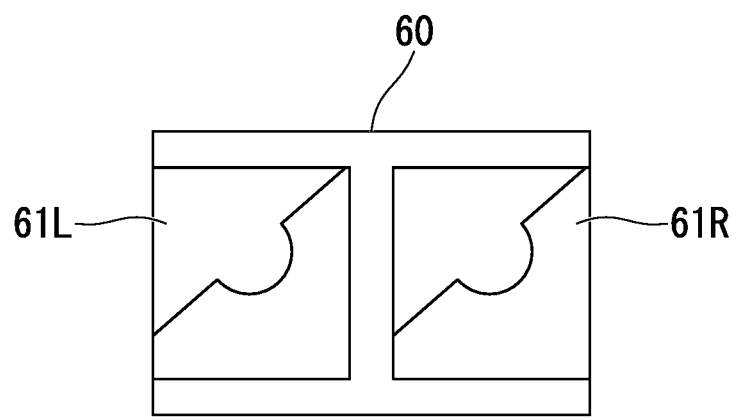
FIG. 8 is a reference view showing an image in the first embodiment of the present invention.

FIG. 8 shows the image that is displayed on the display unit 33 in ST210 and is the same as the image shown in FIG. 6A. In ST210, as shown in FIG. 8, the image including the parallactic images corresponding to the left and right field-of-view areas is displayed. In ST210, the two parallactic images may be enlarged to such an extent that neither parallactic image is hidden on the liquid crystal monitor 6, and then be displayed in parallel.

Subsequently, in ST202, the control unit 43 determines whether or not the manipulation input is performed via the manipulation unit 31. The image (still image) displayed in ST210 is not changed until the manipulation input is performed. In ST202, when the button 70 referring to proceeding to the next processing is manipulated, processing of ST205 is performed.

In ST205, as described above, the image including the parallactic image corresponding to the left field-of-view area is displayed on the display unit 33. When the processing of ST205 is completed, the processing of ST106 (image confirmation processing) is completed, and the processing of ST107 is performed. Further, in ST202, when the manipulation input referring to stopping confirmation of the image is performed, the processing of ST101 is performed, and the endoscopic apparatus 1 operates in the image display mode.

Since the two parallactic images are simultaneously displayed when the image is confirmed as described above, a user can easily compare these images, and readily confirm the validity of the measurement result.

When the image is confirmed, after the two parallactic images are displayed in turn (FIGS. 6B to 6E), further the two parallactic images may be simultaneously displayed (FIG. 8). In addition, both displaying the two parallactic images in turn and displaying the two parallactic images simultaneously may be performed. In addition, after displaying the two parallactic images simultaneously, further the two parallactic images may be displayed in turn. For example, when the image is confirmed, the image 50b of FIG. 6C, the image 50c of FIG. 6D, and the image 60 of FIG. 8 may be displayed on the display unit 33 in turn.

When the two parallactic images are displayed simultaneously, the displayed parallactic images become small, and it is difficult to confirm the parallactic images. However, with the aforementioned method, when only one of the two parallactic images is displayed, the user may confirm the parallactic image in detail, and when both of the two parallactic images are displayed, the user may compare both. Regardless of displaying the two parallactic images simultaneously or separately, at least part of each parallactic image may be configured to be enlarged.

When the image is confirmed, image processing for assisting with the confirmation may be performed on the displayed image, and the image may be displayed. For example, under control of the control unit 43, the image processing unit 34 performs edge reinforcement on the image signal for one frame corresponding to one or both of the two pieces of image information stored in the image storage unit 42, or performs processing of discriminating a halation portion within the image and emphasizing the discriminated area in a predetermined color (e.g., red), thereby outputting the processed image signal to the signal conversion unit 38 as the output image signal 101A. Afterwards, an image is displayed on the display unit 33 by the aforementioned processing. Whether or not the image processing for assisting with the confirmation is performed may be configured to be switched by simple manipulation of a user. This image processing is performed, and thereby the user can easily confirm the validity of the measurement result.

When the image is confirmed, the two parallactic images may be automatically displayed in turn regardless of the manipulation input of the user. For example, like a slide show, the displayed parallactic images may be switched at regular time intervals. The time intervals at which the parallactic images are switched may be configured to be able to be arbitrarily set within a time range within which the user can confirm the images.

In the present embodiment, the example in which the image including the two subject images simultaneously formed by the two optical systems has been described. However, even when an image including three or more subject images corresponding to different points of view is taken, the image may be confirmed by the user in sequences similar to those of the present embodiment.

As described above, according to the present embodiment, since the moving image including only one of the left and right parallactic images is displayed in the image display mode, the visibility when the subject is observed can be secured. Further, since all the left and right parallactic images used for the measurement are displayed as the still images in the image confirmation mode, the validity of the measurement result can be easily confirmed by the user before the measurement is performed.

Second Embodiment

Next, a second embodiment of the present invention will be described. The endoscopic apparatus according to the first embodiment photographs the image including the two subject images simultaneously formed by the two optical systems. However, the endoscopic apparatus according to the second embodiment photographs an image separately including two subject images formed in time series by two optical systems.

Figure 9:
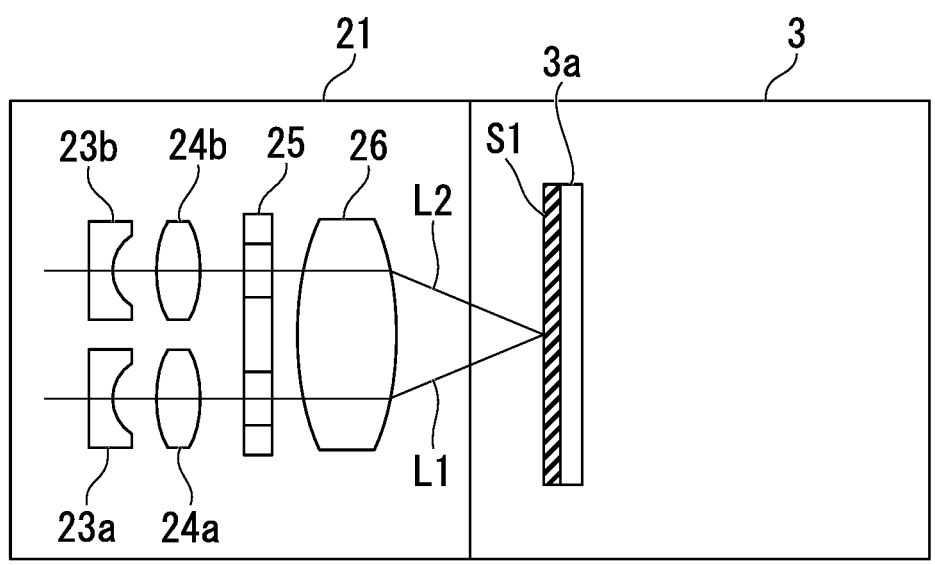
FIG. 9 is a block diagram showing a configuration of an optical adapter mounted on a distal end of an endoscope insertion part of an endoscopic apparatus according to a second embodiment of the present invention.

In the present embodiment, in place of the optical adapter for stereo measurement 2 in the first embodiment, an optical adapter capable of switching an optical path of light incident on the image pickup element is mounted on the distal end of the endoscope insertion part 3. FIG. 9 shows a configuration of the optical adapter in the present embodiment. The optical adapter 21 is mounted on the distal end of the endoscope insertion part 3. The optical adapter 21 includes concave lenses 23a and 23b, convex lenses 24a and 24b, a switching unit 25, and an image-forming optical system 26. An image pickup element 3a is disposed inside the distal end of the endoscope insertion part 3.

The concave lens 23a, the convex lens 24a, and the image-forming optical system 26 constitute a first optical system that causes a first subject image which light from a subject forms to be formed on an area S1 of the image pickup element 3a. The concave lens 23b, the convex lens 24b, and the image-forming optical system 26 constitute a second optical system that causes a second subject image which the light from the subject forms to be formed on the area S1 of the image pickup element 3a. The light from the subject which is incident on the first optical system passes through an optical path L1, and forms an image on the area S1 of the image pickup element 3a as the first subject image. The light from the subject which is incident on the second optical system passes through an optical path L2, and forms an image on the common area S1 of the image pickup element 3a as the second subject image. The first and second subject images are formed on the common area S1 of the image pickup element 3a.

The switching unit 25 switches the optical path between the optical path L1 and the optical path L2 such that only one of the first and second subject images is formed on the area S1. The switching operation of the optical path caused by the switching unit 25 is controlled by a CPU 10 inside a control unit 4. When the optical path L1 is set by the switching unit 25, the image pickup element 3a generates a first image including the first subject image formed on the area S1. When the optical path L2 is set by the switching unit 25, the image pickup element 3a generates a second image including the second subject image formed on the area S1.

The first image has parallax with respect to the second image, or the second image has parallax with respect to the first image. The first image corresponds to the parallactic image of the left field-of-view area in the first embodiment, and the second image corresponds to the parallactic image of the right field-of-view area in the second embodiment. The first and second images generated by the image pickup element 3a are output to the control unit 4.

Figure 10:
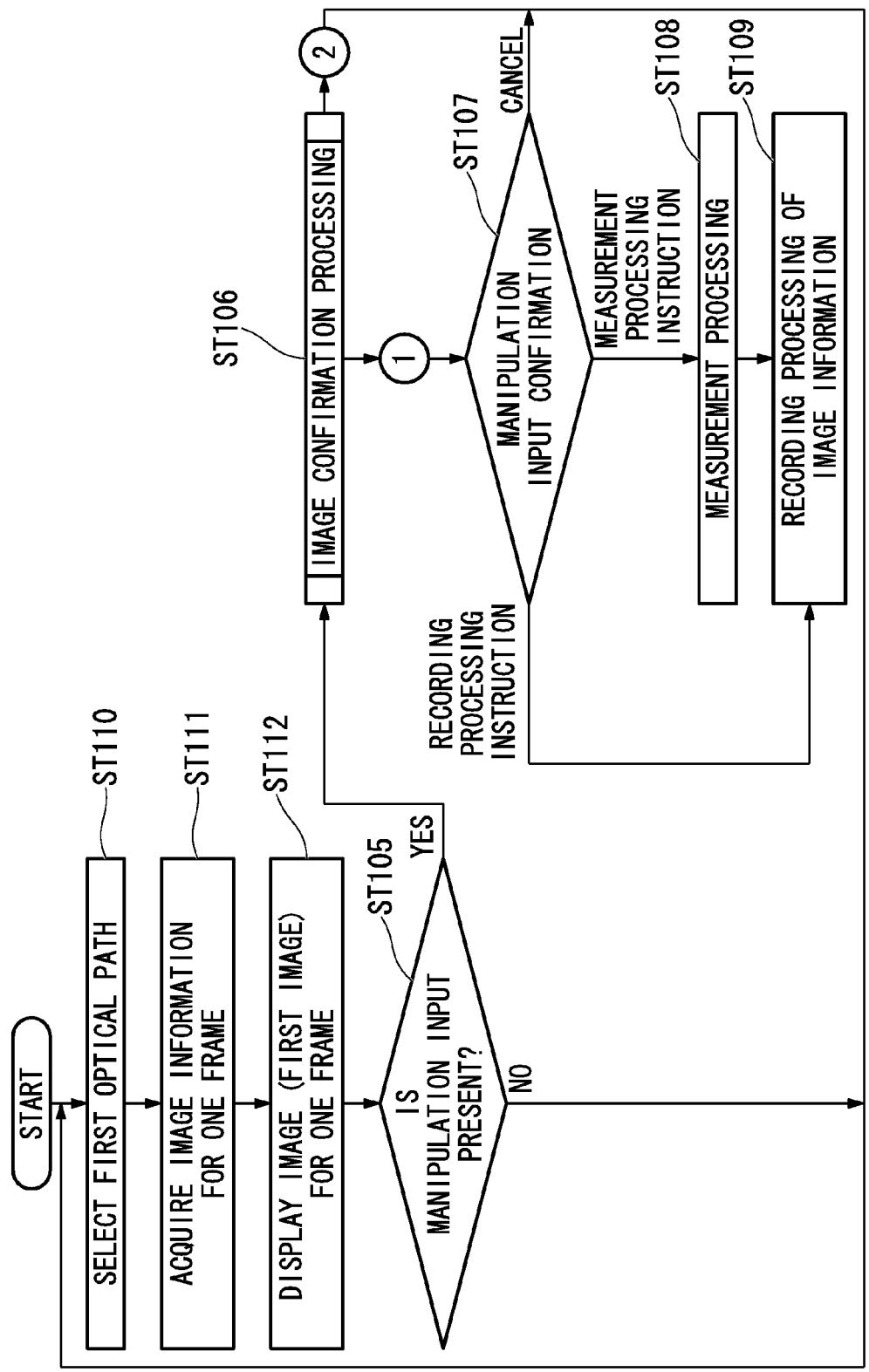
FIG. 10 is a flow chart showing sequences of an operation of the endoscopic apparatus according to the second embodiment of the present invention.
Figure 11:
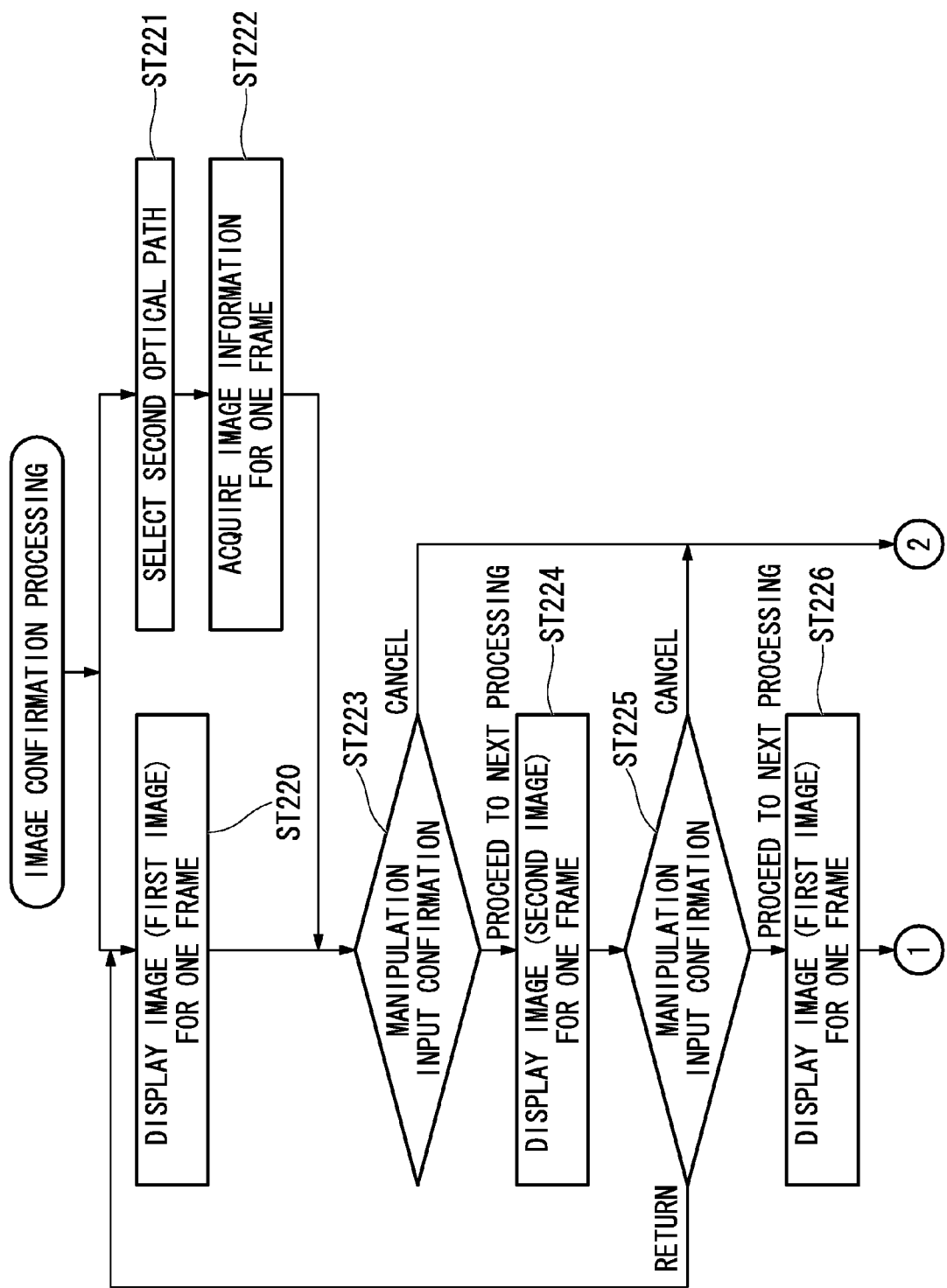
FIG. 11 is a flow chart showing sequences of an operation of the endoscopic apparatus according to the second embodiment of the present invention.

The two subject images which the lights passing through the two optical paths form are formed on the common area S1 of the image pickup element 3a. For this reason, an imaging area may be increased, and a quality of a taken image and precision of measurement may be improved. Next, an operation of the endoscopic apparatus 1 will be described. FIGS. 10 and 11 show sequences of the operation of the endoscopic apparatus 1. As shown in FIG. 10, in ST110, under control of the control unit 43, the switching unit 25 sets an optical path to the optical path L1. Subsequently, in ST111, the control unit 4 acquires image information for one frame from the image generation unit 30. That is, under control of the control unit 43, an input image signal 100 is output from the image generation unit 30 to the image processing unit 34 of the control unit 4, and the input image signal 100 for one frame is acquired as the image information by the image processing unit 34. The image processing unit 34 performs predetermined image processing on the acquired input image signal 100, and outputs the processed input image signal 100 to the signal conversion unit 38 as an output image signal 101A as well as to the image storage unit 42 as an output image signal 101B. The output image signal 101B output to the image storage unit 42 is stored in the image storage unit 42 as first image information.

Figure 12A:
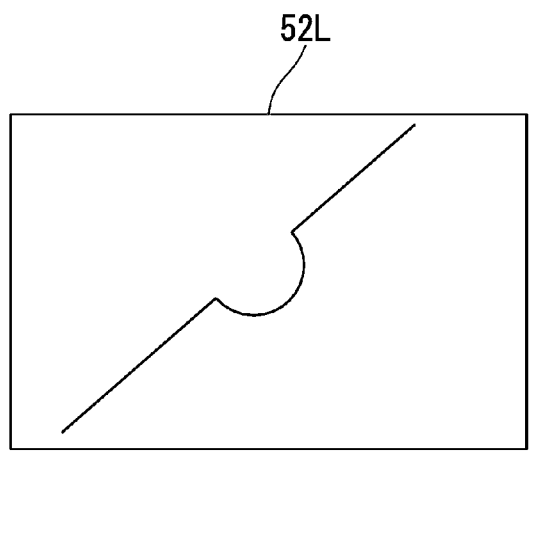
FIG. 12A is a reference view showing an image in the second embodiment of the present invention.

Subsequently, in ST112, under control of the control unit 43, the signal conversion unit 38 performs processing on the output image signal 101A that has been input thereto such as changing an image size to a size at which the display unit 33 can display an image, and outputs the processed output image signal 101A to the display unit 33 as a display image signal 101a. The display unit 33 displays an image based on the display image signal 101a. Thereby, the first image is displayed on the display unit 33. FIGS. 12A, 12B, 12C, and 12D show images displayed by the endoscopic apparatus 1 of the present embodiment. FIG. 12A shows an image displayed on the display unit 33 in ST112, wherein a first image 52L based on the light passing through the optical path L1 is displayed.

When the processing of ST112 is completed, processing of ST105 is performed. Processing of ST105 to ST109 is similar to that described in the first embodiment, except for processing of ST106. As such, description of such processing will be omitted. Next, the processing (image confirmation processing) performed in ST106 will be described in detail. FIG. 11 shows sequences of the processing performed in ST106. As shown in FIG. 11, in ST220, under control of the control unit 43, the image processing unit 34 outputs an image signal for one frame corresponding to the first image information stored in the image storage unit 42 to the signal conversion unit 38 as the output image signal 101A. Under control of the control unit 43, the signal conversion unit 38 performs processing on the output image signal 101A that has been input thereto such as changing an image size to a size at which the display unit 33 can display an image, and outputs the processed output image signal 101A to the display unit 33 as the display image signal 101a. The display unit 33 displays an image based on the display image signal 101a. Thereby, the first image is displayed on the display unit 33. The first image displayed in ST220 is the same as the first image previously displayed in ST112.

Figure 12B:
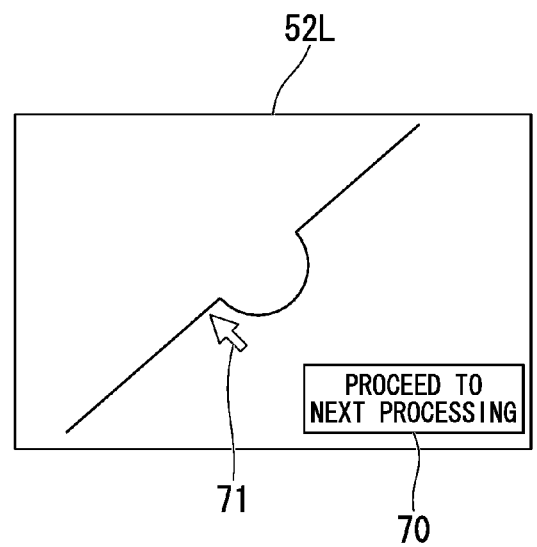
FIG. 12B is a reference view showing an image in the second embodiment of the present invention.

FIG. 12B shows an image displayed on the display unit 33 in ST220, wherein a first image 52L based on the light passing through the optical path L1, a button 70 for manipulation input, and a cursor 71 for a user manipulating the button 70 are displayed. Information such as a letter indicating whether either of the first and second images is displayed may be displayed along with the image.

In parallel with the processing of ST220, processing of ST221 and processing of ST222 are performed. In ST221, under control of the control unit 43, the switching unit 25 sets an optical path to the optical path L2. Subsequently, in ST222, the control unit 4 acquires image information for one frame from the image generation unit 30. That is, under control of the control unit 43, the input image signal 100 is output from the image generation unit 30 to the image processing unit 34 of the control unit 4, and the input image signal 100 for one frame is acquired as the image information by the image processing unit 34. The image processing unit 34 performs predetermined image processing on the acquired input image signal 100, and outputs the processed input image signal 100 to the image storage unit 42 as the output image signal 101B. The output image signal 101B output to the image storage unit 42 is stored in the image storage unit 42 as the second image information.

Subsequently, in ST223, the control unit 43 determines whether or not the manipulation input is performed via the manipulation unit 31. The image (still image) displayed in ST220 is not changed until the manipulation input is performed. In ST223, when the manipulation input referring to proceeding to the next processing is performed, processing of ST224 is performed.

In ST224, under control of the control unit 43, the image processing unit 34 outputs an image signal for one frame corresponding to the second image information stored in the image storage unit 42 to the signal conversion unit 38 as the output image signal 101A. Afterwards, an image is displayed on the display unit 33 by the aforementioned processing. Thereby, the second image is displayed on the display unit 33. Information such as a letter indicating whether either of the first and second images is displayed may be displayed along with the image.

Figure 12C:
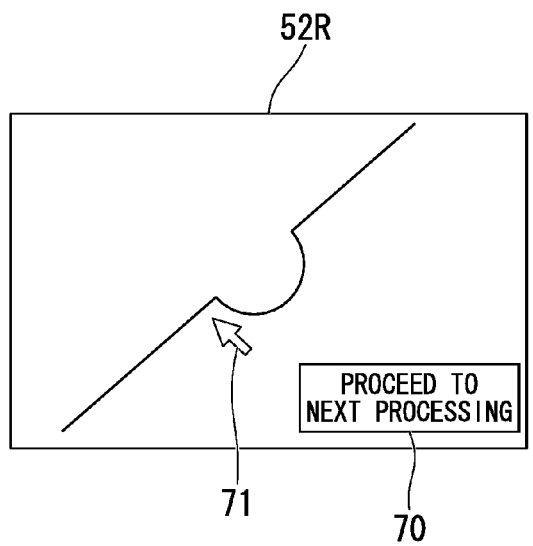
FIG. 12C is a reference view showing an image in the second embodiment of the present invention.

FIG. 12C shows an image displayed on the display unit 33 in ST224, wherein a second image 52R based on the light passing through the optical path L2, a button 70 for manipulation input, and a cursor 71 for a user manipulating the button 70 are displayed. Information such as a letter indicating whether either of the first and second images is displayed may be displayed along with the image.

Subsequently, in ST225, the control unit 43 determines whether or not the manipulation input is performed via the manipulation unit 31. The image (still image) displayed in ST224 is not changed until the manipulation input is performed. In ST225, when the manipulation input referring to proceeding to the next processing is performed, processing of ST226 is performed.

Like ST220, in ST226, the first image is displayed on the display unit 33, In ST226, the second image may be displayed. When the processing of ST226 is completed, the processing of ST106 (image confirmation processing) is completed, and processing of ST107 is performed. Further, in ST225, when the manipulation input referring to returning to the previous processing is performed, the processing of ST220 is performed, and the image including the parallactic image corresponding to the left field-of-view area is displayed on the display unit 33 again. In this case, processing of ST221 and processing of ST222 are not performed. Further, in ST223 and ST225, when the manipulation input referring to stopping confirmation of the image is performed, the processing of ST110 is performed, and the endoscopic apparatus 1 operates in the image display mode.

Figure 12D:
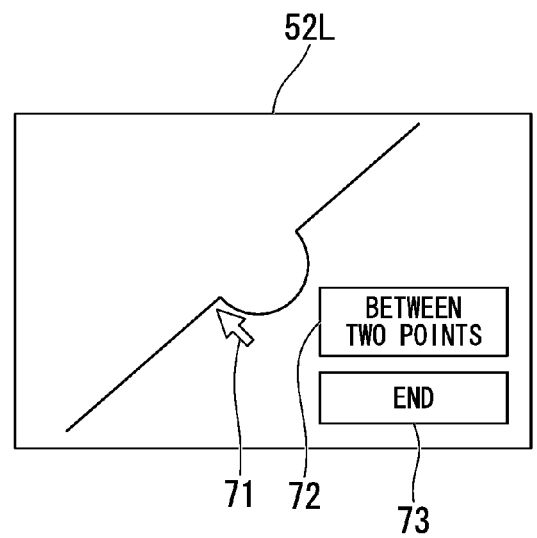
FIG. 12D is a reference view showing an image in the second embodiment of the present invention.

In ST108 (measurement processing), measurement is performed using the first and second images. FIG. 12D shows an image displayed on the display unit 33 in ST108, wherein a first image 52L based on the light passing through the optical path L1, a button 72 for manipulation input for a user instructing a start of calculation processing of measurement after input of a measurement point, a button 73 for manipulation input for a user instructing an end of measurement processing, and a cursor 71 for a user designating the measurement point or manipulating the buttons 72 and 73 are included. In FIG. 12D, the first image is displayed, but the second image may be displayed.

As described above, except for the event of the confirmation of the image (ST106), the image is displayed based on the light passing through only one of the two optical paths. For this reason, when two images are simultaneously displayed based on the lights passing through the two respective optical paths, the reduction in visibility caused by frequent shifting of the user's eyes between the two parallactic images does not occur. Further, in the image confirmation mode, since all the images used for the measurement are confirmed by the processing of ST220 and the processing of ST224, the user may easily confirm the validity of the measurement result before the measurement is performed.

Figure 13:
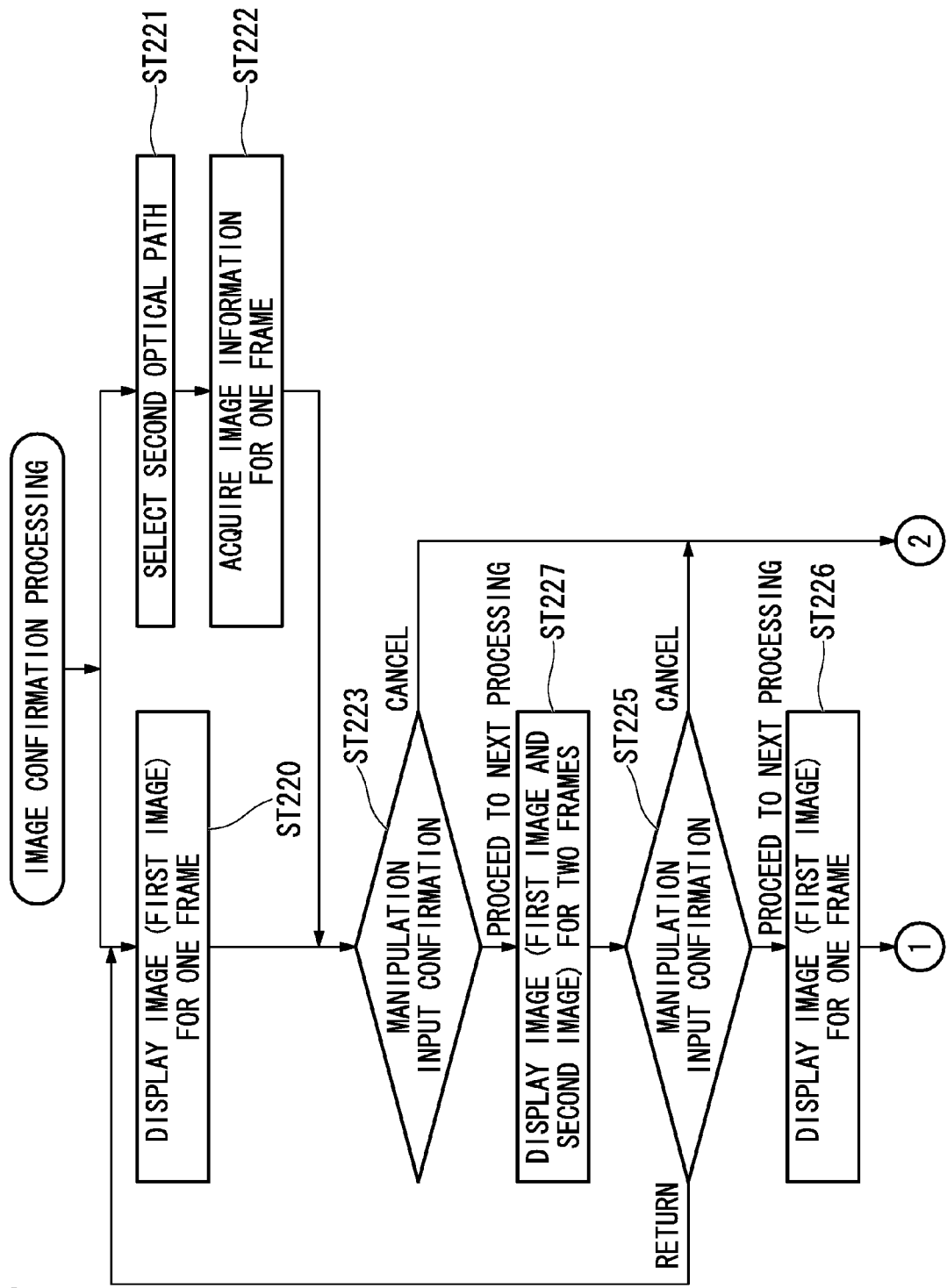
FIG. 13 is a flow chart showing sequences of an operation of the endoscopic apparatus according to the second embodiment of the present invention.

Next, a modification of the present embodiment will be described. FIG. 13 shows another example of the sequences of the processing performed in ST106. In FIG. 13, the processing that is performed in ST224 shown in FIG. 11 is modified into processing performed in ST227 described below.

In ST227, under control of the control unit 43, the image processing unit 34 combines an image signal for one frame corresponding to the first image information and an image signal for one frame corresponding to the second image information, both of which are stored in the image storage unit 42 such that two images are displayed in parallel, and outputs the combined image signal to the signal conversion unit 38 as the output image signal 101A. Afterwards, an image is displayed on the display unit 33 by the aforementioned processing. Thereby, the first and second images are displayed on the display unit 33.

Figure 14:
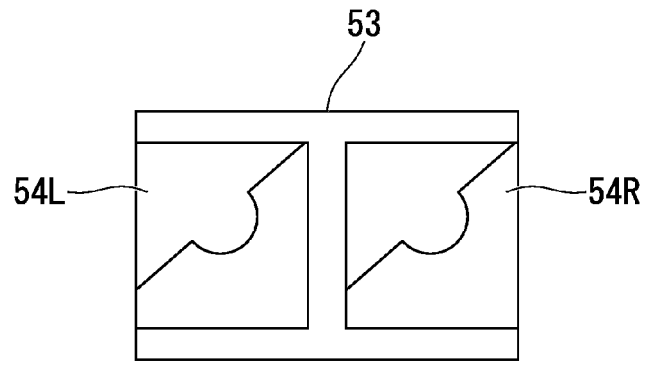
FIG. 14 is a reference view showing an image in the second embodiment of the present invention.

FIG. 14 shows an image displayed on the display unit 33 in ST227. An image 53 includes a first image 54L in which the first image is contracted based on the light passing through the optical path L1 and a second image 54R in which the second image is contracted based on the light passing through the optical path L2.

In FIG. 13, the processing other than the processing of ST227 has already been described, and so descriptions thereof will be omitted.

When the image is confirmed, after the two images are displayed in turn (FIGS. 12A to 12D), further the two images may be simultaneously displayed (FIG. 14). In addition, both displaying the two parallactic images in turn and displaying the two parallactic images simultaneously may be performed. In addition, after displaying the two parallactic images simultaneously, further the two parallactic images may be displayed in turn. For example, when the image is confirmed, the image 52L of FIG. 12B, the image 52R of FIG. 12C, and the image 53 of FIG. 14 may be displayed on the display unit 33 in turn.

Further, as described in the first embodiment, when the image is confirmed, image processing for assisting the confirmation may be performed on the displayed image, and the image may be displayed. When the image is confirmed, the two images may be automatically displayed in turn regardless of the manipulation input of the user.

In the present embodiment, the example in which the image separately including the two subject images formed in time series by the two optical systems has been described. However, even when an image including three or more subject images corresponding to different points of view is taken, the image may be confirmed by the user in sequences similar to those of the present embodiment.

Further, the present embodiment can be applied to an apparatus that sequentially projects a plurality of patterns on the test object and performs the measurement using a plurality of images in which the respective patterns are photographed. For example, before a function of the measurement is activated, a moving image (moving image based on one subject image) in which the test object for observation is photographed is displayed. When the photographing for the measurement is instructed, a plurality of patterns are projected and photographed on the test object, and a plurality of images (still images based on one subject image) used for the measurement are generated. Afterwards, all the images used for the measurement are displayed as still images in turn or simultaneously, and are confirmed by a user. After all the images are completely confirmed, a measurement point is input, and the measurement is performed.

As described above, according to the present embodiment, in the endoscopic apparatus that photographs the image separately including the two subject images formed in time series by the two optical systems, the visibility when the subject is observed can be secured in the image display mode, and the validity of the measurement result can be easily confirmed by the user in the image confirmation mode before the measurement is performed.

Third Embodiment

Next, a third embodiment of the present invention will be described. In the present embodiment, a case in which a recorded image is reproduced to perform measurement will be described. Hereinafter, a method of causing a user to confirm an image used for measurement taking a case in which the measurement is performed on a personal computer 17 by way of example will be described.

For example, a file including all pieces of image information used for measurement is recorded on the personal computer 17 by the processing of ST109 (recording processing of the image information). In this case, information showing the image information (hereinafter referred to as "representative image information") representative of all pieces of recorded image information is also recorded on the file. In the processing of ST109, the file may be recorded on an external storage medium such as a card medium that is connected to the endoscopic apparatus 1. The external storage medium may be connected to the personal computer 17, and the file may be read into the personal computer 17.

Figure 15:
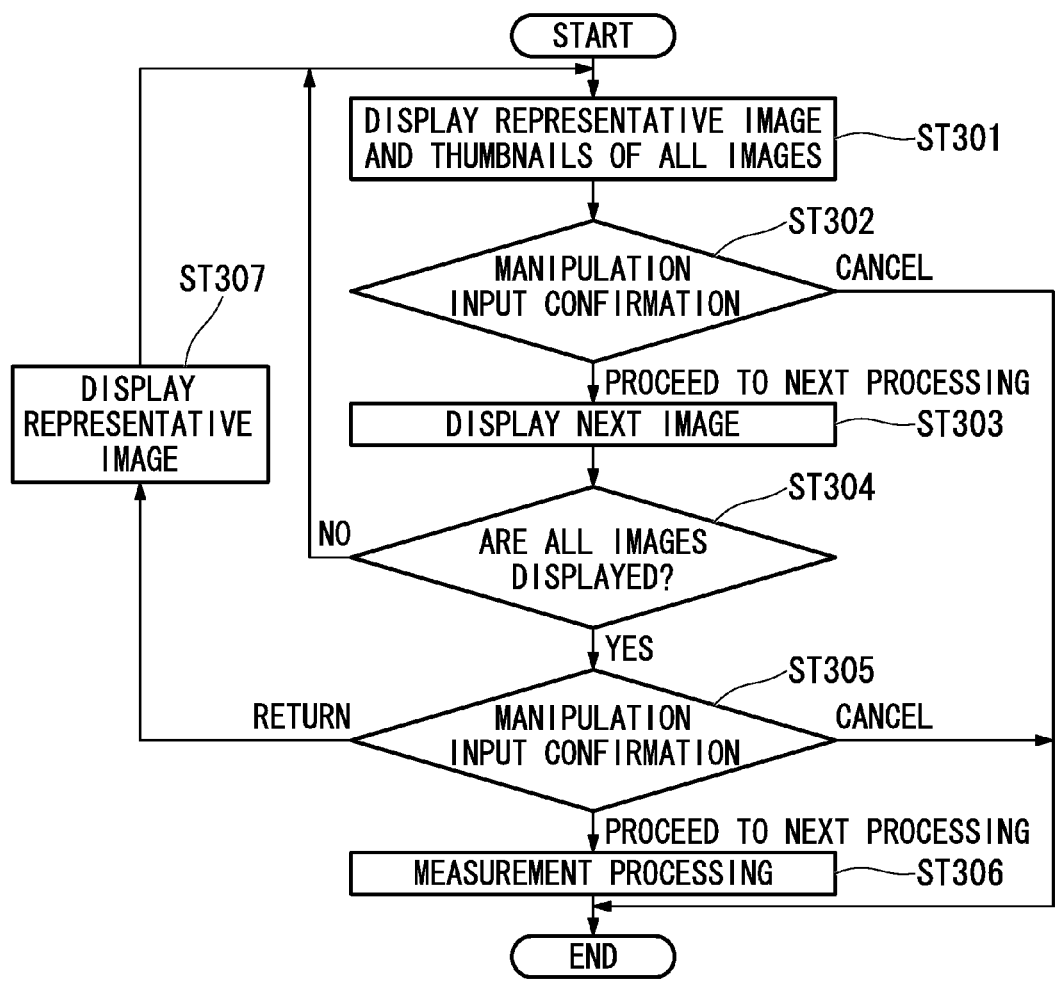
FIG. 15 is a flow chart showing sequences of an operation of an endoscopic apparatus according to a third embodiment of the present invention.

After the file is recorded on the personal computer 17, the confirmation of the image and the measurement are performed in the sequence shown in FIG. 15 when a user opens the file on the personal computer 17. FIG. 15 shows sequences of an operation of a control unit of the personal computer 17.

Figure 16:
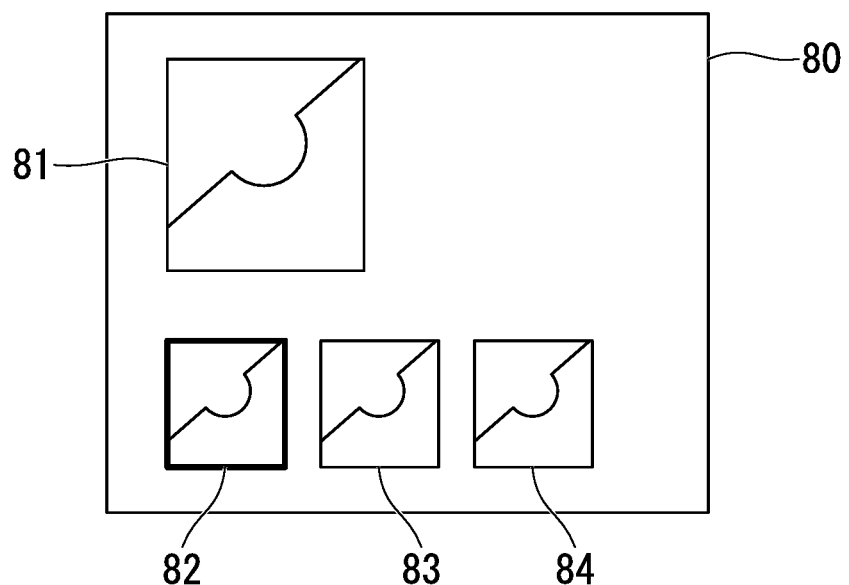
FIG. 16 is a reference view showing a screen when an image is confirmed in the third embodiment of the present invention.

As shown in FIG. 15, in ST301, the control unit displays an image (hereinafter referred to as "representative image") on a display unit of the personal computer 17 based on the representative image information, and displays thumbnails of all pieces of image information recorded on the file. FIG. 16 shows a screen of the display unit of the personal computer 17 when a user confirms an image. A still image 81 for confirmation, and thumbnails 82, 83, and 84 that are contracted images of the image information recorded on the file are displayed on the screen 80 of the display unit. In FIG. 16, a case in which an image including three subject images corresponding to different points of view is photographed simultaneously or in time series, and three images corresponding to the three respective subject images are generated is shown as an example. However, it is sufficient if two or more images are generated.

In ST301, the representative image is displayed as the still image 81. Further, the thumbnail 82 corresponding to the still image 81 is highlighted and displayed. In FIG. 16, the thumbnail 82 is the thumbnail of the representative image. In the example shown in FIG. 16, the thumbnails 82, 83, and 84 are displayed. However, when the image is confirmed, the thumbnails 82, 83, and 84 may not be displayed.

Subsequently, in ST302, the control unit determines whether or not the manipulation input is performed on the personal computer 17. The image (still image) displayed in ST301 is not changed until the manipulation input is performed. In ST302, when the manipulation input referring to proceeding to the next step is performed, processing of ST303 is performed.

In ST303, the control unit displays another still image different from the displayed still image on the display unit. For example, in ST301, when the image corresponding to the thumbnail 82 of FIG. 16 is displayed as the still image 81, the image corresponding to the thumbnail 83 in ST303 is displayed as the still image 81, and the image corresponding to the thumbnail 83 in ST301 is displayed as the still image 81. In this case, the image corresponding to the thumbnail 84 is ST303 is displayed as the still image 81. The image (still image) displayed in ST303 is not changed until the next manipulation input is performed.

Subsequently, in ST304, the control unit determines whether or not all the images in the same file are displayed as the still images. When no image is displayed as the still image, the processing of ST302 is performed again. Further, when all the images are displayed as the still images, processing of ST305 is performed.

In ST305, the control unit determines whether or not the manipulation input is performed on the personal computer 17. In ST305, when the manipulation input referring to proceeding to the next step is performed, processing of ST306 is performed. In ST306, the control unit performs measurement processing. In the measurement processing, an image for measurement including the representative image and a menu for measurement is displayed on the display unit, and a measurement point is input. Further, in the measurement processing, a size (a distance between two points, a depth, an area, etc.) of the subject at a designated measurement point is measured using the representative image information and all pieces of image information corresponding to the still image displayed in ST303. When the measurement processing is completed, the processing of the confirmation and measurement of the image is completed.

Further, in ST305, when the manipulation input referring to returning to the previous processing is performed, processing of ST307 is performed. In ST307, the control unit returns the still image displayed on the display unit to the representative image, and performs the processing of ST302 again. Further, in ST302 and ST305, when the manipulation input referring to stopping confirmation of the image is performed, the processing of the confirmation and measurement of the image is completed.

In the present embodiment, the method of reproducing the recorded image to perform the measurement using the apparatus other than the endoscopic apparatus 1 has been described. However, the image may be reproduced to perform the measurement on the endoscopic apparatus 1 by a method similar to the aforementioned method. As described above, according to the present embodiment, even when the recorded image is reproduced to perform the measurement, since all the images used for the measurement are displayed as the still images, the validity of the measurement result can be easily confirmed by the user before the measurement is performed.

While exemplary embodiments of the invention have been described, the invention is not limited to these embodiments. It will be understood by those skilled in the art that various additions, omissions, substitutions, and other modifications in configurations may be made therein without departing from the spirit and scope of the invention. Accordingly, the invention is not to be seen as limited by the foregoing description, but is only limited by the scope of the appended claims.

What is claimed is:

1. An endoscopic apparatus comprising:
    an image generation unit configured to generate an image including one or more subject images;
    a display unit configured to display the image; and
    a control unit configured to control measurement of a size of a subject based on the image,
    wherein the control unit is configured to perform:
        first processing of displaying a moving image including one subject image on the display unit,
        second processing of, after the first processing, displaying (i) all of a plurality of subject images used for the measurement, or (ii) all of a plurality of images based on one subject image used for the measurement, on the display unit as still images, all of the plurality of subject images used for the measurement and all of the plurality of images based on the one subject image used for the measurement being acquired in time series,
        third processing of, after the second processing, transferring to the second processing again based on a first instruction of a user, and
        fourth processing of, after the third processing, designating a measurement point based on a second instruction of the user, and measuring the size of the subject at the designated measurement point based on (i) an image based on all of the plurality of subject images used for the measurement, or (ii) all of the plurality of images based on the one subject image used for the measurement.

2. The endoscopic apparatus according to claim 1, wherein, in the second processing, the control unit respectively displays all of the plurality of subject images used for the measurement on the display unit in time series as the still images.

3. The endoscopic apparatus according to claim 1, wherein, in the second processing, the control unit respectively displays all of the plurality of images based on the one subject image used for the measurement on the display unit in time series as the still images.

4. The endoscopic apparatus according to claim 1, wherein, in the second processing, the control unit simultaneously displays all of the plurality of subject images used for the measurement on the display unit as the still images.

5. The endoscopic apparatus according to claim 1, wherein, in the second processing, the control unit simultaneously displays all of the plurality of images based on the one subject image used for the measurement on the display unit as the still images.

6. The endoscopic apparatus according to claim 1, wherein, in the second processing, the control unit simultaneously displays all of the plurality of subject images used for the measurement on the display unit as the still images after respectively displaying all of the plurality of subject images used for the measurement on the display unit in time series as the still images.

7. The endoscopic apparatus according to claim 1, wherein, in the second processing, the control unit simultaneously displays all of the plurality of images based on the one subject image used for the measurement on the display unit as the still images after respectively displaying all of the plurality of images based on the one subject image used for the measurement on the display unit in time series as the still images.

8. The endoscopic apparatus according to claim 1, wherein, in the second processing, the control unit respectively displays all of the plurality of subject images used for the measurement on the display unit in time series as the still images after simultaneously displaying all of the plurality of subject images used for the measurement on the display unit as the still images.

9. The endoscopic apparatus according to claim 1, wherein, in the second processing, the control unit respectively displays all of the plurality of images based on the one subject image used for the measurement on the display unit in time series as the still images after simultaneously displaying all of the plurality of images based on the one subject image used for the measurement on the display unit as the still images.

10. The endoscopic apparatus according to claim 1, wherein, in the second processing, the control unit displays images, which are obtained by performing image processing on all of the plurality of subject images used for the measurement, on the display unit as the still images.

11. The endoscopic apparatus according to claim 1, wherein, in the second processing, the control unit displays images, which are obtained by performing image processing on all of the plurality of images based on the one subject image used for the measurement, on the display unit as the still images.

12. The endoscopic apparatus according to claim 10, wherein the control unit controls whether or not to perform the image processing.

13. The endoscopic apparatus according to claim 1, wherein the control unit is further configured to perform processing for ending the measurement based on an operation by the user.

14. The endoscopic apparatus according to claim 1, wherein the still images that are displayed when transferring to the second processing again based on the first instruction of the user are newly photographed images.

15. A measuring method comprising:
    a first step of displaying a moving image including one subject image photographed by an endoscopic apparatus on a display unit;
    a second step of, after the first step, displaying (i) all of a plurality of subject images used for measurement, or (ii) all of a plurality of images based on one subject image used for measurement, on the display unit as still images, all of the plurality of subject images used for the measurement and all of the plurality of images based on the one subject image used for the measurement being acquired in time series;
    a third step of, after the second step, transferring to the second step again based on a first instruction of a user; and
    a fourth step of, after the third step, designating a measurement point based on a second instruction of the user, and measuring a size of a subject at the designated measurement point based on (i) an image based on all of the plurality of subject images, or (ii) all of the plurality of images based on the one subject image used for measurement.

16. An endoscopic apparatus comprising:
an image generation unit configured to generate an image including subject images;
a display unit configured to display the image; and
a control unit configured to control measurement of a size of a subject based on the image,
wherein the control unit is configured to perform:
   first processing of displaying a moving image including one subject image on the display unit,
   second processing of, after the first processing, displaying all of a plurality of images used for the measurement on the display unit as still images, all of the plurality of images used for the measurement being acquired in time series,
   third processing of, after the second processing, transferring to the second processing again based on a first instruction of a user, and
   fourth processing of, after the third processing, designating a measurement point based on a second instruction of the user, and measuring the size of the subject at the designated measurement point based on all of the plurality of images used for the measurement.

\* \* \* \* \*